US010561587B2

(12) United States Patent
Koide et al.

(10) Patent No.: US 10,561,587 B2
(45) Date of Patent: *Feb. 18, 2020

(54) COMPOSITION IN THE FORM OF NANO- OR MICRO-EMULSION

(71) Applicant: L'OREAL, Paris (FR)

(72) Inventors: Maki Koide, Kawasaki (JP); Anne-Laure Bernard, New York, NY (US)

(73) Assignee: L'OREAL, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 15/129,961

(22) PCT Filed: Mar. 31, 2015

(86) PCT No.: PCT/JP2015/060685
§ 371 (c)(1),
(2) Date: Sep. 28, 2016

(87) PCT Pub. No.: WO2015/152420
PCT Pub. Date: Oct. 8, 2015

(65) Prior Publication Data
US 2017/0156998 A1 Jun. 8, 2017

(30) Foreign Application Priority Data
Apr. 1, 2014 (JP) ................. 2014-075670

(51) Int. Cl.
A61K 8/06 (2006.01)
A61K 8/34 (2006.01)
A61K 8/37 (2006.01)
A61K 8/39 (2006.01)
A61K 8/42 (2006.01)
A61K 8/45 (2006.01)
A61K 8/46 (2006.01)
A61K 8/49 (2006.01)
A61K 8/68 (2006.01)
A61K 8/73 (2006.01)
A61K 8/92 (2006.01)
A61Q 1/14 (2006.01)
A61K 8/362 (2006.01)
A61Q 19/00 (2006.01)

(52) U.S. Cl.
CPC .............. A61K 8/062 (2013.01); A61K 8/06 (2013.01); A61K 8/068 (2013.01); A61K 8/34 (2013.01); A61K 8/345 (2013.01); A61K 8/362 (2013.01); A61K 8/37 (2013.01); A61K 8/39 (2013.01); A61K 8/42 (2013.01); A61K 8/45 (2013.01); A61K 8/463 (2013.01); A61K 8/4993 (2013.01); A61K 8/68 (2013.01); A61K 8/73 (2013.01); A61K 8/92 (2013.01); A61Q 1/14 (2013.01); A61Q 19/00 (2013.01); A61K 2800/262 (2013.01); A61K 2800/596 (2013.01)

(58) Field of Classification Search
CPC ... A61K 8/06; A61K 8/34; A61K 8/37; A61K 8/39; A61K 8/42; A61K 8/45; A61K 8/46; A61K 8/49
See application file for complete search history.

(56) References Cited

U.S. PATENT DOCUMENTS

| 2,528,378 | A | 10/1950 | Mannheimer |
| 2,781,354 | A | 2/1957 | Mannheimer |
| 5,364,633 | A | 11/1994 | Hill et al. |
| 5,411,744 | A | 5/1995 | Hill et al. |
| 5,618,523 | A | 4/1997 | Zysman et al. |
| 5,665,778 | A | 9/1997 | Semeria et al. |
| 5,773,611 | A | 6/1998 | Zysman et al. |
| 5,869,711 | A | 2/1999 | Philippe et al. |
| 5,959,127 | A | 9/1999 | Semeria et al. |
| 6,001,376 | A | 12/1999 | Mahieu et al. |
| 6,039,936 | A * | 3/2000 | Restle ............ A61K 8/06 424/401 |
| 6,039,939 | A | 3/2000 | Ley et al. |
| 6,039,963 | A | 3/2000 | Philippe et al. |
| 6,210,691 | B1 | 4/2001 | Mahieu et al. |
| 8,394,755 | B2 * | 3/2013 | Andjelic ............ A61K 8/39 510/505 |
| 2001/0023514 | A1 | 9/2001 | Cottard et al. |

(Continued)

FOREIGN PATENT DOCUMENTS

| CN | 1303666 A | 7/2001 |
| CN | 101267804 A | 9/2008 |

(Continued)

OTHER PUBLICATIONS

International Search Report and Written Opinion for PCT/JP2015/060685, dated Jul. 10, 2015.
Davies, J.T., "A Quantitative Kenetic Theory of Emulsion Type. I. Physical Chemistry of the Emulsifying Agent," Reprinted from: Gas/Liquid and Liquid/Liquid Interfaces, Proceedings of 2nd International Congress Surface Activity, Butterworths, London, 1957, pp. 426-438.
L'Oreal, "Body Expertise Body Care Range," Mintel, XP-002740990, Database Accession No. 123056, Nov. 2001.
Perrin et al., "13 Emulsions Stabilized by Polyelectrolytes," Physical Chemistry of Polyelectrolytes, Surfactant Science Series, vol. 99, 2001, pp. 383-384.

(Continued)

Primary Examiner — Shirley V Gembeh
(74) Attorney, Agent, or Firm — The Marbury Law Group, PLLC

(57) ABSTRACT

The present invention relates to a composition in the form of a nano- or micro-emulsion, comprising: (a) at least one oil; (b) at least one nonionic surfactant with an HLB value of from 8.0 to 14.0, preferably from 9.0 to 13.5, and more preferably from 10.0 to 13.0; (c) at least one ceramide compound; (d) at least one anionic surfactant; and (e) water. The composition can be used as a cosmetic composition and provides an excellent feeling during use and can be transparent or slightly translucent, and is stable over time, even at an elevated temperature.

19 Claims, No Drawings

(56) References Cited

U.S. PATENT DOCUMENTS

| | | | |
|---|---|---|---|
| 2003/0185773 A1 | 10/2003 | Love et al. | |
| 2004/0155161 A1 | 6/2004 | Oyama et al. | |
| 2004/0180029 A1* | 9/2004 | Maubru | A61K 8/463 424/70.21 |
| 2005/0281763 A1 | 12/2005 | Suginaka | |
| 2006/0078525 A1 | 4/2006 | Tomokuni | |
| 2006/0110415 A1* | 5/2006 | Gupta | A61K 8/0212 424/401 |
| 2007/0098655 A1 | 5/2007 | Schmaus et al. | |
| 2007/0128146 A1 | 6/2007 | Fujino et al. | |
| 2010/0047296 A1 | 2/2010 | Banowski et al. | |
| 2010/0266510 A1* | 10/2010 | Tamarkin | A61K 8/046 424/43 |
| 2011/0052512 A1 | 3/2011 | Monello | |
| 2013/0039992 A1 | 2/2013 | Thompson | |
| 2015/0141508 A1 | 5/2015 | Klug et al. | |

FOREIGN PATENT DOCUMENTS

| | | |
|---|---|---|
| CN | 101401775 A | 4/2009 |
| CN | 101536962 A | 9/2009 |
| CN | 101919791 A | 12/2010 |
| CN | 102014661 A | 4/2011 |
| CN | 102525843 A | 7/2012 |
| CN | 102784084 A | 11/2012 |
| DE | 4402929 C1 | 6/1995 |
| DE | 4420736 C1 | 8/1995 |
| DE | 4424530 A1 | 1/1996 |
| DE | 4424533 A1 | 1/1996 |
| EP | 0227994 A1 | 7/1987 |
| EP | 0487958 A1 | 6/1992 |
| EP | 0646572 A1 | 4/1995 |
| EP | 0647617 A1 | 4/1995 |
| EP | 0736522 A1 | 10/1996 |
| FR | 2673179 A1 | 8/1992 |
| JP | 09-110635 A | 4/1997 |
| JP | 11-71256 A | 3/1999 |
| JP | 11-071256 A | 3/1999 |
| JP | 2003-300855 A | 10/2003 |
| JP | 2005-520849 A | 7/2005 |
| JP | 2005-343864 A | 12/2005 |
| JP | 2006-117643 A | 5/2006 |
| JP | 2006-249011 A | 9/2006 |
| JP | 2006-312622 A | 11/2006 |
| JP | 2006-321769 A | 11/2006 |
| JP | 2006-526005 A | 11/2006 |
| JP | 2006-335693 A | 12/2006 |
| JP | 2009-023947 A | 2/2009 |
| JP | 2009-286735 A | 12/2009 |
| JP | 2009-298748 A | 12/2009 |
| JP | 2010-030910 A | 2/2010 |
| JP | 2010-143858 A | 7/2010 |
| JP | 2010-229068 A | 10/2010 |
| JP | 2012-229193 A | 11/2012 |
| JP | 2013-049633 A | 3/2013 |
| JP | 2013-170154 A | 9/2013 |
| JP | 2014-101294 A | 6/2014 |
| JP | 2014-114256 A | 6/2014 |
| WO | 94/07844 A1 | 4/1994 |
| WO | 94/10131 A1 | 5/1994 |
| WO | 94/24097 A1 | 10/1994 |
| WO | 95/16665 A1 | 6/1995 |
| WO | 95/23807 A1 | 9/1995 |
| WO | 02/078650 A1 | 10/2002 |
| WO | 2009/075142 A | 6/2009 |
| WO | 2012/079938 A1 | 6/2012 |
| WO | 2013/178683 A2 | 12/2013 |
| WO | 2015/099198 A1 | 7/2015 |

OTHER PUBLICATIONS

Notification received in connection with international application No. PCT/JP2015/060685; dated Jul. 30, 2016.
Japanese Office Action for counterpart Application JP2014-075670, dated Apr. 16, 2018.
Notification of Third Party Observation for counterpart JP Application No. 2014-130219, dated May 7, 2018 (with translation).
Japanese Office Action for counterpart JP Application No. 2014-130219, dated Jun. 4, 2018 (with translation).
Suzuki, "Basics on Emulsion Technologies Were Reviewed From the Following Viewpoints," J. Soc. Cosmet. Chem. Jpn., vol. 44, No. 2, pp. 103 and 104 (with English Abstract).
Non-Final Office Action for co-pending U.S. Appl. No. 15/312,432, dated Feb. 23, 2018.
International Search Report and Written Opinion for PCT/JP2015/067379, dated Aug. 26, 2015.
Partial translation of Chinese Office Action for counterpart Application No. 201580017621.3, dated Jan. 2, 2019 (Search Report Only).
Chinese Office Action for counterpart Application No. 201580031613.4, dated Jul. 12, 2019 with translation.

\* cited by examiner

COMPOSITION IN THE FORM OF NANO- OR MICRO-EMULSION

CROSS REFERENCE TO RELATED APPLICATIONS

This is a national stage application of PCT/JP2015/060685, filed internationally on Mar. 31, 2015, which claims priority to Japanese Application No. 2014-075670, filed on Apr. 1, 2014, both of which are incorporated herein by reference in their entireties.

TECHNICAL FIELD

The present invention relates to a composition in the form of a nano- or micro-emulsion, including a ceramide compound. In a particular embodiment, the present invention relates to a cosmetic composition in the form of a nano- or micro-emulsion, including a ceramide compound.

BACKGROUND ART

Ceramide, which is present in the horny layer of the skin, forms a lipid barrier necessary for retaining moisture and plays an important role in the maintaining of moisture in the skin.

Ceramide in the horny layer is produced by the breakdown of cerebroside by an enzyme known as cerebrosidase. The ceramide is partially transformed into phytosphingosine and sphingosine by an enzyme known as ceramidase. Phytosphingosine and sphingosine play an important role in the control of cell growth and differentiation. Six different types of ceramides possessing different functions are present in the human skin.

However, since ceramides are highly crystalline, have a low solubility in other oil components, and produce crystals at a low temperature, it is difficult to ensure long-term stability of cosmetics comprising a ceramide.

Oil-in-water (O/W) or Water-in-oil (W/O) emulsions are well known in the field of cosmetics and dermatology, in particular for the preparation of cosmetic products, such as milks, creams, tonics, serums or toilet waters.

In particular, a fine emulsion such as an O/W nano- or micro-emulsion is particularly interesting in cosmetic products due to its transparent or, slightly translucent aspect.

For example, JP-A-H09-110635 discloses a fine emulsion which is formed by using a combination of polyglyceryl fatty acid ester, as a surfactant, and $C_{10}$-$C_{22}$ 2-hydroxy fatty acid. In addition, JP-A-H11-71256 discloses a fine emulsion which is formed by using a combination of polyglyceryl fatty acid ester and a betain.

However, in order to prepare a fine emulsion including ceramide, in general, a large amount of a surfactant is required, which impairs safety and feeling during use.

If the amount of surfactant is decreased in order to obtain an excellent feeling during use, the ceramide does not solubilize transparently, resulting in a cloudy or opaque emulsion in many cases. In these cases, separation and creaming occur over time and it is difficult to obtain adequate long-term stability, in particular at an elevated temperature.

DISCLOSURE OF INVENTION

An objective of the present invention is to provide a stable composition including a ceramide compound in the form of a nano- or micro-emulsion with transparent or slightly translucent, preferably transparent, aspect of the emulsion, even with a relatively low amount of a surfactant and/or at an elevated temperature.

The above objective of the present invention can be achieved by a composition in the form of a nano- or micro-emulsion, comprising:
(a) at least one oil;
(b) at least one nonionic surfactant with an HLB value of from 8.0 to 14.0, preferably from 9.0 to 13.5, and more preferably from 10.0 to 13.0;
(c) at least one ceramide compound;
(d) at least one anionic surfactant; and
(e) water.

The (a) oil may be selected from the group consisting of oils of plant origin, mineral oils, synthetic oils, silicone oils and hydrocarbon oils. Preferably, the (a) oil may be chosen from ester oils or hydrocarbon oils which are in the form of a liquid at a room temperature. It may be preferable that the (a) oil be chosen from oils with a molecular weight below 600 g/mol.

The amount of the (a) oil may range from 0.1 to 30% by weight, preferably from 0.5 to 20% by weight, and more preferably from 1 to 10% by weight, relative to the total weight of the composition.

The (b) nonionic surfactant may be chosen from:
surfactants that are fluid at a temperature of less than or equal to 45° C., chosen from the esters of at least one polyol chosen from the group formed by polyethylene glycol comprising from 1 to 60 ethylene oxide units, sorbitan, glycerol comprising from 2 to 30 ethylene oxide units, polyglycerols comprising from 2 to 12 glycerol units, and of at least one fatty acid comprising at least one saturated or unsaturated, linear or branched $C_8$-$C_{22}$ alkyl chain, mixed esters of fatty acid or of fatty alcohol, of carboxylic acid and of glycerol, fatty acid esters of sugars and fatty alcohol ethers of sugars, surfactants that are solid at a temperature of less than or equal to 45° C., chosen from fatty esters of glycerol, fatty esters of sorbitan and oxyethylenated fatty esters of sorbitan, ethoxylated fatty ethers and ethoxylated fatty esters, block copolymers of ethylene oxide (A) and of propylene oxide (B), polyoxyethylenated (1-40 EO) and polyoxypropylenated (1-30 PO) alkyl ($C_{16}$-$C_{30}$) ethers, and silicone surfactants.

It is preferable that the (b) nonionic surfactant be chosen from:
polyethylene glycol isostearate or oleate (8 to 10 mol of ethylene oxide),
polyethylene glycol isocetyl, behenyl ether or isostearyl ether (8 to 10 mol of ethylene oxide),
polyglyceryl monolaurate or dilaurate comprising 3 to 6 glycerol units,
polyglyceryl mono(iso)stearate comprising 3 to 6 glycerol units,
polyglyceryl monooleate comprising 3 to 6 glycerol units, and
polyglyceryl dioleate comprising 3 to 6 glycerol units.

The (b) nonionic surfactant may be chosen from polyglyceryl fatty acid esters, preferably esters of a fatty acid and polyglycerine comprising 70% or more of polyglycerine whose polymerization degree is 4 or more, preferably esters of a fatty acid and polyglycerine containing equal to or more than 60% of polyglycerine whose polymerization degree is between 4 and 11, and more preferably esters of a fatty acid and polyglycerine containing equal to or more than 30% of polyglycerine whose polymerization degree is 5.

The amount of the (b) nonionic surfactant may range from 0.1 to 30% by weight, preferably from 0.5 to 20% by weight, and more preferably from 1 to 10% by weight, relative to the total weight of the composition.

The weight ratio of the (b) nonionic surfactant to the (a) oil may be 2 or less, preferably 1.5 or less, and more preferably from 1.0 or less.

The (c) ceramide compound may be represented by formula (I):

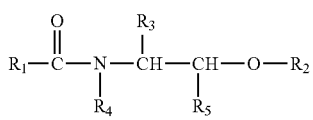

wherein
$R_1$ denotes:
either a saturated or unsaturated and linear or branched $C_1$-$C_{50}$, preferably $C_5$-$C_{50}$, hydrocarbon radical, it being possible for this radical to be substituted by one or more hydroxyl groups optionally esterified by an acid $R_7COOH$, $R_7$ being an optionally mono- or polyhydroxylated, saturated or unsaturated and linear or branched $C_1$-$C_{35}$ hydrocarbon radical, it being possible for the hydroxyl or hydroxyls of the $R_7$ radical to be esterified by an optionally mono- or polyhydroxylated, saturated or unsaturated and linear or branched $C_1$-$C_{35}$ fatty acid;
or an R''—(NR—CO)—R' radical, in which R denotes a hydrogen atom or a mono- or polyhydroxylated, preferably monohydroxylated, $C_1$-$C_{20}$ hydrocarbon radical, R' and R'' are hydrocarbon radicals, the sum of the carbon atoms of which is between 9 and 30, R' being a divalent radical;
or an $R_8$—O—CO—$(CH_2)_p$ radical, in which $R_8$ denotes a $C_1$-$C_{20}$ hydrocarbon radical and p is an integer varying from 1 to 12;
$R_2$ is chosen from a hydrogen atom, a radical of saccharide type, in particular a (glycosyl), (galactosyl)$_m$ or sulphogalactosyl radical, a sulphate or phosphate residue, a phosphorylethylamine radical and a phosphorylethylammonium radical, in which n is an integer varying from 1 to 4 and m is an integer varying from 1 to 8;
$R_3$ denotes a hydrogen atom or a hydroxylated or nonhydroxylated and saturated or unsaturated $C_1$-$C_{33}$ hydrocarbon radical, it being possible for the hydroxyl or hydroxyls to be esterified by an inorganic acid or an acid $R_7COOH$, $R_7$ having the same meanings as hereinabove, and it being possible for the hydroxyl or hydroxyls to be etherified by a (glycosyl)$_n$, (galactosyl)$_m$, sulphogalactosyl, phosphorylethylamine or phosphorylethylammonium radical, in which n is an integer varying from 1 to 4 and m is an integer varying from 1 to 8, it also being possible for $R_3$ to be substituted by one or more $C_1$-$C_{14}$ alkyl radicals;
$R_4$ denotes a hydrogen atom, a methyl or ethyl radical, an optionally hydroxylated, saturated or unsaturated and linear or branched $C_3$-$C_{50}$ hydrocarbon radical or a —$CH_2$—CHOH—$CH_2$—O—$R_6$ radical, in which $R_6$ denotes a $C_{10}$-$C_{26}$ hydrocarbon radical, or an $R_8$—O—CO—$(CH_2)_p$ radical, in which $R_8$ denotes a $C_1$-$C_{20}$ hydrocarbon radical and p is an integer varying from 1 to 12;

$R_5$ denotes a hydrogen atom or an optionally mono- or polyhydroxylated, saturated or unsaturated and linear or branched $C_1$-$C_{30}$ hydrocarbon radical, it being possible for the hydroxyl or hydroxyls to be etherified by a (glycosyl)$_n$, (galactosyl)$_m$, sulphogalactosyl, phosphorylethylamine or phosphorylethylammonium radical, in which n is an integer varying from 1 to 4 and m is an integer varying from 1 to 8;
with the proviso that, when $R_3$ and $R_5$ denote hydrogen or when $R_3$ denotes hydrogen and $R_5$ denotes methyl, then $R_4$ does not denote a hydrogen atom or a methyl or ethyl radical.

It is preferable that, in the above formula (I), $R_3$ denote a $C_{15}$-$C_{26}$ α-hydroxyalkyl radical, the hydroxyl group optionally being esterified by a $C_{16}$-$C_{30}$ α-hydroxy acid.

It is preferable that the (c) ceramide compound be selected from the group consisting of 2-N-linoleoylaminooctadecane-1,3-diol, 2-N-oleoylaminooctadecane-1,3-diol, 2-N-palmitoylaminooctadecane-1,3-diol, 2-N-stearoylaminooctadecane-1,3-diol, 2-N-behenoylaminooctadecane-1,3-diol, 2-N-[2-hydroxypalmitoyl]aminooctadecane-1,3-diol, 2-N-stearoylaminooctadecane-1,3,4-triol, 2-N-palmitoylaminohexadecane-1,3-diol, and mixtures thereof.

It is also preferable that the (c) ceramide compound be chosen from bis(N-hydroxyethyl-N-cetyl)malonamide, the N-(2-hydroxyethyl)-N-(3-cetyloxy-2-hydroxypropyl)amide of cetylic acid and N-docosanoyl-N-methyl-D-glucamine.

The amount of the (c) ceramide compound may range from 0.01 to 20% by weight, preferably from 0.1 to 15% by weight, and more preferably from 0.1 to 10% by weight, relative to the total weight of the composition.

The weight ratio of the (b) nonionic surfactant to the (c) ceramide compound may be 15 or less, preferably 10 or less, and more preferably from 6 or less.

The (d) anionic surfactant may be selected from anionic derivatives of proteins of vegetable origin or of silk proteins, phosphates and alkyl phosphates, carboxylates, sulphosuccinates, amino acid derivatives, alkyl sulphates, alkyl ether sulphates, sulphonates, isethionates, taurates, alkyl sulphoacetates, polypeptides, anionic derivatives of alkyl polyglucosides, and their mixtures.

It is preferable that the (d) anionic surfactant be selected from taurates or glutamates, and preferably sodium N-stearoyl-N-methyl-taurate.

The amount of the (d) anionic surfactant may range from 0.01 to 20% by weight, preferably from 0.05 to 10% by weight, and more preferably from 0.1 to 5% by weight, relative to the total weight of the composition.

The amount of the (e) water may range from 40 to 90% by weight or more, preferably from 50 to 85% by weight, and more preferably from 60 to 80% by weight relative to the total weight of the composition.

It may be preferable that the composition according to the present invention further comprise at least one cationic or amphoteric surfactant.

It is preferable that the composition according to the present invention have the turbidity of 300 or less, preferably 200 or less, and more preferably 100 or less.

Further, the present invention also relates to a non-therapeutic process for treating the skin, the hair, mucous membranes, the nails, the eyelashes, the eyebrows and/or the scalp, characterized in that the composition according to the present invention is applied to the skin, the hair, mucous membranes, the nails, the eyelashes, the eyebrows or the scalp.

Furthermore, the present invention also relates to a use of the composition according to the present invention, as it is or in care products and/or washing products and/or make-up products and/or make-up-removing products, for body and/or facial skin and/or mucous membranes and/or the scalp and/or the hair and/or the nails and/or the eyelashes and/or the eyebrows.

BEST MODE FOR CARRYING OUT THE INVENTION

After diligent research, the inventors have found that it is possible to provide a stable composition including a ceramide compound in the form of a nano- or micro-emulsion with transparent or slightly translucent, preferably transparent, aspect of the emulsion, even with a relatively low amount of a surfactant and/or at an elevated temperature.

Thus, the first aspect of the present invention is a composition in the form of a nano- or micro-emulsion, comprising:
(a) at least one oil;
(b) at least one nonionic surfactant with an HLB value of from 8.0 to 14.0, preferably from 9.0 to 13.5, and more preferably from 10.0 to 13.0;
(c) at least one ceramide compound;
(d) at least one anionic surfactant; and
(e) water.

The composition according to the present invention has a dispersed phase which has a smaller diameter due to a combination of the nonionic surfactant(s) with an HLB value of from 8.0 to 14.0 and the anionic surfactant(s), even with a relatively low amount of each surfactant.

The composition according to the present invention including a ceramide compound can have an excellent feeling during use and can be in the form of a nano- or micro-emulsion which is transparent or slightly translucent, and is stable over time, even at an elevated temperature.

Since the composition according to the present invention can have transparent or slightly translucent, the composition can be preferably used for lotions and the like. Further, as the dispersed phase is finely dispersed, the composition according to the present invention can provide unique texture, moisturizing and wet feeling, as well as increased suppleness. Furthermore, if the dispersed phase is an oil phase and includes one or more ceramide compounds, the dispersed oil phase can function as a carrier of the ceramide compound(s) and accelerate the penetration of the ceramide compound(s) into the skin, or can distribute the ceramide compound(s) on the skin.

Hereafter, the composition according to the present invention and the cosmetic process according to the present invention will each be described in a detailed manner.
[Composition]
(Oil)

The composition according to the present invention comprises at least one oil. Here, "oil" means a fatty compound or substance which is in the form of a liquid at room temperature (25° C.) under atmospheric pressure (760 mmHg). As the (a) oil(s), those generally used in cosmetics can be used alone or in combination thereof. The oil(s) may be volatile or non-volatile, preferably non-volatile.

The (a) oil may be a non-polar oil such as a hydrocarbon oil, a silicone oil, or the like; a polar oil such as a plant or animal oil and an ester oil or an ether oil; or a mixture thereof.

It is preferable that the (a) oil be selected from the group consisting of oils of plant or animal origin, synthetic oils, silicone oils and hydrocarbon oils.

As examples of plant oils, mention may be made of, for example, linseed oil, *camellia* oil, macadamia nut oil, corn oil, mink oil, olive oil, avocado oil, sasanqua oil, castor oil, safflower oil, jojoba oil, sunflower oil, almond oil, rapeseed oil, sesame oil, soybean oil, peanut oil, and mixtures thereof.

As examples of animal oils, mention may be made of, for example, squalene and squalane.

As examples of synthetic oils, mention may be made of alkane oils such as isododecane and isohexadecane, ester oils, ether oils and artificial triglycerides.

The ester oils are preferably liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total number of carbon atoms of the esters being greater than or equal to 10.

Preferably, for the esters of monoalcohols, at least one from among the alcohol and the acid from which the esters of the invention are derived is branched.

Among the monoesters of monoacids and of monoalcohols, mention may be made of ethyl palmitate, ethyl hexyl palmitate, isopropyl palmitate, dicaprylyl carbonate, alkyl myristates such as isopropyl myristate or ethyl myristate, isocetyl stearate, 2-ethylhexyl isononanoate, isononyl isononanoate, isodecyl neopentanoate and isostearyl neopentanoate.

Esters of $C_4$-$C_{22}$ dicarboxylic or tricarboxylic acids and of $C_1$-$C_{22}$ alcohols and esters of monocarboxylic, dicarboxylic or tricarboxylic acids and of non-sugar $C_4$-$C_{26}$ dihydroxy, trihydroxy, tetrahydroxy or pentahydroxy alcohols may also be used.

Mention may especially be made of: diethyl sebacate; isopropyl lauroyl sarcosinate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis(2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; diethylene glycol diisononanoate.

As ester oils, one can use sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may have one to three conjugated or non-conjugated carbon-carbon double bonds.

The esters according to this variant may also be selected from monoesters, diesters, triesters, tetraesters and polyesters, and mixtures thereof.

These esters may be, for example, oleates, laurates, palmitates, myristates, behenates, cocoates, stearates, linoleates, linolenates, caprates and arachidonates, or mixtures thereof such as, especially, oleopalmitate, oleostearate and palmitostearate mixed esters, as well as pentaerythrityl tetraethyl hexanoate.

More particularly, use is made of monoesters and diesters and especially sucrose, glucose or methylglucose monooleates or dioleates, stearates, behenates, oleopalmitates, linoleates, linolenates and oleostearates.

An example that may be mentioned is the product sold under the name Glucate® DO by the company Amerchol, which is a methylglucose dioleate.

As examples of preferable ester oils, mention may be made of, for example, diisopropyl adipate, dioctyl adipate, 2-ethylhexyl hexanoate, ethyl laurate, cetyl octanoate, octyldodecyl octanoate, isodecyl neopentanoate, myristyl propionate, 2-ethylhexyl 2-ethylhexanoate, 2-ethylhexyl octanoate, 2-ethylhexyl caprylate/caprate, methyl palmitate, ethyl palmitate, isopropyl palmitate, ethylhexyl palmitate, isohexyl laurate, hexyl laurate, isocetyl stearate, isopropyl isostearate, isopropyl myristate, isodecyl oleate, glyceryl tri(2-ethylhexanoate), pentaerythrithyl tetra(2-ethylhexanoate), 2-ethylhexyl succinate, diethyl sebacate, and mixtures thereof.

As examples of ether oils, mention may be made of, for example, dicaprylylether and diisocetylether.

As examples of artificial triglycerides, mention may be made of, for example, glyceryl trimyristate, glyceryl tripalmitate, glyceryl trilinolenate, glyceryl trilaurate, glyceryl tricaprate, glyceryl tricaprylate, glyceryl tri(caprate/caprylate) and glyceryl tri(caprate/caprylate/linolenate).

As examples of silicone oils, mention may be made of, for example, linear organopolysiloxanes such as dimethylpolysiloxane, methylphenylpolysiloxane, methylhydrogenpolysiloxane, and the like; cyclic organopolysiloxanes such as octamethylcyclotetrasiloxane, decamethylcyclopentasiloxane, dodecamethylcyclohexasiloxane, and the like; and mixtures thereof.

Preferably, silicone oil is chosen from liquid polydialkylsiloxanes, especially liquid polydimethylsiloxanes (PDMS) and liquid polyorganosiloxanes comprising at least one aryl group.

These silicone oils may also be organomodified. The organomodified silicones that can be used in accordance with the present invention are silicone oils as defined above and comprising in their structure one or more organofunctional groups attached via a hydrocarbon-based group.

Organopolysiloxanes are defined in greater detail in Walter Noll's *Chemistry and Technology of Silicones* (1968), Academic Press. They may be volatile or non-volatile.

Volatile or non-volatile silicone oils, such as volatile or non-volatile polydimethylsiloxanes (PDMS) containing a linear or cyclic silicone chain, that are liquid or pasty at ambient temperature, in particular cyclopolydimethylsiloxanes (cyclomethicones) such as cyclohexasiloxane; polydimethylsiloxanes containing alkyl, alkoxy or phenyl groups that are pendent or at the end of the silicone chain, which groups have from 2 to 24 carbon atoms; phenyl silicones such as phenyl trimethicones, phenyl dimethicones, phenyltrimethylsiloxydiphenylsiloxanes, diphenyl dimethicones, diphenylmethyldiphenyltrisiloxanes; 2-phenylethyltrimethyl siloxysilicates, and polymethylphenylsiloxanes, may be used.

Hydrocarbon oils may be chosen from:
linear or branched, optionally cyclic, $C_6$-$C_{16}$ lower alkanes. Examples that may be mentioned include hexane, undecane, dodecane, tridecane, and isoparaffins, for instance isohexadecane, isododecane and isodecane; and
linear or branched hydrocarbons containing more than 16 carbon atoms, such as liquid paraffins, liquid petroleum jelly, polydecenes and hydrogenated polyisobutenes such as Parleam®, and squalane.

As preferable examples of hydrocarbon oils, mention may be made of, for example, linear or branched hydrocarbons such as mineral oil (e.g., liquid paraffin), paraffin, vaseline or petrolatum, naphthalenes, and the like; hydrogenated polyisobutene, isoeicosan, and decene/butene copolymer; and mixtures thereof.

The (a) oil may be a fatty alcohol. The term "fatty alcohol" here means any saturated or unsaturated, linear or branched $C_8$-$C_{30}$ alcohol, which is optionally substituted, in particular with one or more hydroxyl groups (in particular 1 to 4). If they are unsaturated, these compounds may comprise one to three conjugated or non-conjugated carbon-carbon double bonds.

Among the $C_8$-$C_{30}$ fatty alcohols, $C_{12}$-$C_{30}$ fatty alcohols, for example, may be used. Mention may be made, among these, of lauryl alcohol, cetyl alcohol, stearyl alcohol, isostearyl alcohol, oleyl alcohol, behenyl alcohol, linoleyl alcohol, undecylenyl alcohol, palmitoleyl alcohol, linolenyl alcohol, myristyl alcohol, arachidonyl alcohol, erucyl alcohol, octyldodecanol, and mixtures thereof.

It is preferable that the (a) oil be chosen from ester oils or hydrocarbon oils which are in the form of a liquid at a room temperature.

It is also preferable that the (a) oil be chosen from oils with molecular weight below 600 g/mol.

Preferably, the (a) oil has a low molecular weight such as below 600 g/mol, chosen among ester oils with a short hydrocarbon chain or chains ($C_1$-$C_{12}$) (e.g., isopropyl myristate, isopropyl palmitate, isononyl isononanoate, and ethyl hexyl palmitate), hydrocarbon oils (e.g., isododecane, isohexadecane, and squalane), branched and/or unsaturated fatty alcohol ($C_{12}$-$C_{30}$) type oils such as octyldodecanol and oleyl alcohol, and ether oils such as dicaprylylether.

The amount in the composition according to the present invention of the (a) oil is not limited, and may range from 0.1 to 30% by weight, preferably from 0.5 to 20% by weight, and more preferably from 1 to 10% by weight, relative to the total weight of the composition.

(Nonionic Surfactant)

The composition according to the present invention comprises at least one specific nonionic surfactant. A single type of the specific nonionic surfactant may be used, but two or more different types of the specific nonionic surfactant may be used in combination.

The specific nonionic surfactant has an HLB (Hydrophilic Lipophilic Balance) value of from 8.0 to 14, preferably from 9.0 to 13.5, and more preferably from 10.0 to 13.0. If two or more nonionic surfactants are used, the HLB value is determined by the weight average of the HLB values of all the nonionic surfactants.

The (b) nonionic surfactant with an HLB value of from 8.0 to 14, preferably from 9.0 to 13.5, and more preferably from 10.0 to 13.0 may be chosen from:
(1) surfactants that are fluid at a temperature of less than or equal to 45° C., chosen from the esters of at least one polyol chosen from the group formed by polyethylene glycol comprising from 1 to 60 ethylene oxide units, sorbitan, glycerol comprising from 2 to 30 ethylene oxide units, polyglycerols comprising from 2 to 12 glycerol units, and of at least one fatty acid comprising at least one saturated or unsaturated, linear or branched $C_8$-$C_{22}$ alkyl chain,
(2) mixed esters of fatty acid or of fatty alcohol, of carboxylic acid and of glycerol, (3) fatty acid esters of sugars and fatty alcohol ethers of sugars,
(4) surfactants that are solid at a temperature of less than or equal to 45° C., chosen from fatty esters of glycerol, fatty esters of sorbitan and oxyethylenated fatty esters of sorbitan, ethoxylated fatty ethers and ethoxylated fatty esters,
(5) block copolymers of ethylene oxide (A) and of propylene oxide (B),
(6) polyoxyethylenated (1-40 EO) and polyoxypropylenated (1-30 PO) alkyl ($C_{16}$-$C_{30}$) ethers, and
(7) silicone surfactants.

The surfactants (1) that are fluid at a temperature of less than or equal to 45° C. may be, in particular:

the isostearate of polyethylene glycol of molecular weight 400, sold under the name PEG-400 by the company Unichema;

diglyceryl isostearate, sold by the company Solvay;

glyceryl laurate comprising 2 glycerol units, sold by the company Solvay;

sorbitan oleate, sold under the name Span 80 by the company ICI;

sorbitan isostearate, sold under the name Nikkol SI 10R by the company Nikko; and α-butylglucoside cocoate or α-butylglucoside caprate, sold by the company Ulice.

The (2) mixed esters of fatty acid or of fatty alcohol, of carboxylic acid and of glycerol, which can be used as the above nonionic surfactant, may be chosen in particular from the group comprising mixed esters of fatty acid or of fatty alcohol with an alkyl chain containing from 8 to 22 carbon atoms, and of α-hydroxy acid and/or of succinic acid, with glycerol. The α-hydroxy acid may be, for example, citric acid, lactic acid, glycolic acid or malic acid, and mixtures thereof.

The alkyl chain of the fatty acids or alcohols from which are derived the mixed esters which can be used in the nanoemulsion of the invention may be linear or branched, and saturated or unsaturated. They may especially be stearate, isostearate, linoleate, oleate, behenate, arachidonate, palmitate, myristate, laurate, caprate, isostearyl, stearyl, linoleyl, oleyl, behenyl, myristyl, lauryl or capryl chains, and mixtures thereof.

As examples of mixed esters which can be used in the nanoemulsion of the invention, mention may be made of the mixed ester of glycerol and of the mixture of citric acid, lactic acid, linoleic acid and oleic acid (CTFA name: Glyceryl citrate/lactate/linoleate/oleate) sold by the company Hills under the name Imwitor 375; the mixed ester of succinic acid and of isostearyl alcohol with glycerol (CTFA name: Isostearyl diglyceryl succinate) sold by the company Hills under the name Imwitor 780 K; the mixed ester of citric acid and of stearic acid with glycerol (CTFA name: Glyceryl stearate citrate) sold by the company Hills under the name Imwitor 370; the mixed ester of lactic acid and of stearic acid with glycerol (CTFA name: Glyceryl stearate lactate) sold by the company Danisco under the name Lactodan B30 or Rylo LA30.

The (3) fatty acid esters of sugars, which can be used as the above nonionic surfactant, may preferably be solid at a temperature of less than or equal to 45° C. and may be chosen in particular from the group comprising esters or mixtures of esters of $C_8$-$C_{22}$ fatty acid and of sucrose, of maltose, of glucose or of fructose, and esters or mixtures of esters of $C_{14}$-$C_{22}$ fatty acid and of methylglucose.

The $C_8$-$C_{22}$ or $C_{14}$-$C_{22}$ fatty acids forming the fatty unit of the esters which can be used in the present invention comprise a saturated or unsaturated linear alkyl chain containing, respectively, from 8 to 22 or from 14 to 22 carbon atoms. The fatty unit of the esters may be chosen in particular from stearates, behenates, arachidonates, palmitates, myristates, laurates and caprates, and mixtures thereof. Stearates are preferably used.

As examples of esters or mixtures of esters of fatty acid and of sucrose, of maltose, of glucose or of fructose, mention may be made of sucrose monostearate, sucrose distearate and sucrose tristearate and mixtures thereof, such as the products sold by the company Croda under the name Crodesta F50, F70, F110 and F160; and examples of esters or mixtures of esters of fatty acid and of methylglucose which may be mentioned are methylglucose polyglyceryl-3 distearate, sold by the company Goldschmidt under the name Tego-care 450. Mention may also be made of glucose or maltose monoesters such as methyl o-hexadecanoyl-6-D-glucoside and o-hexadecanoyl-6-D-maltoside.

The (3) fatty alcohol ethers of sugars, which can be used as the above nonionic surfactant, may be solid at a temperature of less than or equal to 45° C. and may be chosen in particular from the group comprising ethers or mixtures of ethers of $C_8$-$C_{22}$ fatty alcohol and of glucose, of maltose, of sucrose or of fructose, and ethers or mixtures of ethers of a $C_{14}$-$C_{22}$ fatty alcohol and of methylglucose. These are in particular alkylpolyglucosides.

The $C_8$-$C_{22}$ or $C_{14}$-$C_{22}$ fatty alcohols forming the fatty unit of the ethers which may be used in the nanoemulsion of the invention comprise a saturated or unsaturated, linear alkyl chain containing, respectively, from 8 to 22 or from 14 to 22 carbon atoms. The fatty unit of the ethers may be chosen in particular from decyl, cetyl, behenyl, arachidyl, stearyl, palmityl, myristyl, lauryl, capryl and hexadecanoyl units, and mixtures thereof, such as cetearyl.

As examples of fatty alcohol ethers of sugars, mention may be made of alkylpolyglucosides such as decylglucoside and laurylglucoside, which is sold, for example, by the company Henkel under the respective names Plantaren 2000 and Plantaren 1200, cetostearyl glucoside optionally as a mixture with cetostearyl alcohol, sold for example, under the name Montanov 68 by the company SEPPIC, under the name Tego-care CG90 by the company Goldschmidt and under the name Emulgade KE3302 by the company Henkel, as well as arachidyl glucoside, for example in the form of a mixture of arachidyl alcohol and behenyl alcohol and arachidyl glucoside, sold under the name Montanov 202 by the company SEPPIC.

The surfactant used more particularly is sucrose monostearate, sucrose distearate or sucrose tristearate and mixtures thereof, methylglucose polyglyceryl-3 distearate and alkylpolyglucosides.

The (4) fatty esters of glycerol which may be used as the above nonionic surfactant, which are solid at a temperature of less than or equal to 45° C., may be chosen in particular from the group comprising esters formed from at least one acid comprising a saturated linear alkyl chain containing from 12 to 22 carbon atoms and from 1 to 12 glycerol units. One or more of these fatty esters of glycerol may be used in the present invention.

These esters may be chosen in particular from stearates, behenates, arachidates and palmitates, and mixtures thereof. Stearates and palmitates are preferably used.

As examples of surfactants which can be used in the present invention, mention may be made of decaglyceryl monostearate, distearate, tristearate and pentastearate (CTFA names: Polyglyceryl-10 stearate, Polyglyceryl-10 distearate, Polyglyceryl-10 tristearate, Polyglyceryl-10 pentastearate), such as the products sold under the respective names Nikkol Decaglyn 1-S, 2-S, 3-S and 5-S by the company Nikko, and diglyceryl monostearate (CTFA name: Polyglyceryl-2 stearate), such as the product sold by the company Nikko under the name Nikkol DGMS.

The (4) fatty esters of sorbitan which may be used as the above nonionic surfactant, which are solid at a temperature of less than or equal to 45° C., may be chosen from the group comprising $C_{16}$-$C_{22}$ fatty acid esters of sorbitan and oxyethylenated $C_{16}$-$C_{22}$ fatty acid esters of sorbitan. They are formed from at least one fatty acid comprising at least one saturated linear alkyl chain containing, respectively, from 16 to 22 carbon atoms, and from sorbitol or from ethoxylated sorbitol. The oxyethylenated esters generally comprise from 1 to 100 ethylene glycol units and preferably from 2 to 40 ethylene oxide (EO) units.

These esters may be chosen in particular from stearates, behenates, arachidates, palmitates, and mixtures thereof. Stearates and palmitates are preferably used.

As examples of the above nonionic surfactant can be used in the present invention, mention may be made of sorbitan monostearate (CTFA name: sorbitan stearate), sold by the company ICI under the name Span 60, sorbitan monopalmitate (CTFA name: sorbitan palmitate), sold by the company ICI under the name Span 40, and sorbitan tristearate 20 EO (CTFA name: polysorbate 65), sold by the company ICI under the name Tween 65.

The (4) ethoxylated fatty ethers that are solid at a temperature of less than or equal to 45° C., which may be used as the above nonionic surfactant, are preferably ethers formed from 1 to 100 ethylene oxide units and from at least one fatty alcohol chain containing from 16 to 22 carbon atoms. The fatty chain of the ethers may be chosen in particular from behenyl, arachidyl, stearyl and cetyl units, and mixtures thereof, such as cetearyl. Examples of ethoxylated fatty ethers which may be mentioned are behenyl alcohol ethers comprising 5, 10, 20 and 30 ethylene oxide units (CTFA names: beheneth-5, beheneth-10, beheneth-20, beheneth-30), such as the products sold under the names Nikkol BBS, BB10, BB20 and BB30 by the company Nikko, and stearyl alcohol ether comprising 2 ethylene oxide units (CTFA name: steareth-2), such as the product sold under the name Brij 72 by the company ICI.

The (4) ethoxylated fatty esters that are solid at a temperature of less than or equal to 45° C., which may be used as the above nonionic surfactant, are esters formed from 1 to 100 ethylene oxide units and from at least one fatty acid chain containing from 16 to 22 carbon atoms. The fatty chain in the esters may be chosen in particular from stearate, behenate, arachidate and palmitate units, and mixtures thereof. Examples of ethoxylated fatty esters which may be mentioned are the ester of stearic acid comprising 40 ethylene oxide units, such as the product sold under the name Myrj 52 (CTFA name: PEG-40 stearate) by the company ICI, as well as the ester of behenic acid comprising 8 ethylene oxide units (CTFA name: PEG-8 behenate), such as the product sold under the name Compritol HD5 ATO by the company Gattefosse.

The (5) block copolymers of ethylene oxide (A) and of propylene oxide (B), which may be used as surfactants in the nanoemulsion according to the invention, may be chosen in particular from block copolymers of formula (I):

(I)

in which x, y and z are integers such that x+z ranges from 2 to 100 and y ranges from 14 to 60, and mixtures thereof, and more particularly from the block copolymers of formula (I) having an HLB value ranging from 8.0 to 14.

The (6) polyoxyethylenated (1-40 EO) and polyoxypropylenated (1-30 PO) alkyl ($C_{16}$-$C_{30}$) ethers which may be used as surfactants in the nanoemulsion according to the invention, may be selected from the group consisting of:

PPG-6 Decyltetradeceth-30; Polyoxyethlene (30) Polyoxypropylene (6) Tetradecyl Ether such as those sold as Nikkol PEN-4630 from Nikko Chemicals Co., PPG-6 Decyltetradeceth-12; Polyoxyethylene (12) Polyoxypropylene (6) Tetradecyl Ether such as those sold as Nikkol PEN-4612 from Nikko Chemicals Co., PPG-13 Decyltetradeceth-24; Polyoxyethylene (24) Polyoxypropylene (13) Decyltetradecyl Ether such as those sold as UNILUBE 50MT-2200B from NOF Corporation, PPG-6 Decyltetradeceth-20; Polyoxyethylene (20) Polyoxypropylene (6) Decyltetradecyl Ether such as those sold as Nikkol PEN-4620 from Nikko Chemicals Co., PPG-4 Ceteth-1; Polyoxyethylene (1) Polyoxypropylene (4) Cetyl Ether such as those sold as Nikkol PBC-31 from Nikko Chemicals Co., PPG-8 Ceteth-1; Polyoxyethylene (1) Polyoxypropylene (8) Cetyl Ether such as those sold as Nikkol PBC-41 from Nikko Chemicals Co., PPG-4 Ceteth-10; Polyoxyethylene (10) Polyoxypropylene (4) Cetyl Ether such as those sold as Nikkol PBC-33 from Nikko Chemicals Co., PPG-4 Ceteth-20; Polyoxyethylene (20) Polyoxypropylene (4) Cetyl Ether such as those sold as Nikkol PBC-34 from Nikko Chemicals Co., PPG-5 Ceteth-20; Polyoxyethylene (20) Polyoxypropylene (5) Cetyl Ether such as those sold as Procetyl AWS from Croda Inc., PPG-8 Ceteth-20; Polyoxyethylene (20) Polyoxypropylene (8) Cetyl Ether such as those sold as Nikkol PBC-44 from Nikko Chemicals Co., and PPG-23 Steareth-34; Polyoxyethylene Polyoxypropylene Stearyl Ether (34 EO) (23 PO) such as those sold as Unisafe 34S-23 from Pola Chemical Industries. They can provide a composition with stability for a long time, even though the temperature of the composition is increased and decreased in a relatively short period of time.

It is more preferable that the polyoxyethylenated (1-40 EO) and polyoxypropylenated (1-30 PO) alkyl ($C_{16}$-$C_{30}$) ethers are (15-40 EO) and polyoxypropylenated (5-30 PO) alkyl ($C_{16}$-$C_{24}$) ethers, which could be selected from the group consisting of PPG-6 Decyltetradeceth-30, PPG-13 Decyltetradeceth-24, PPG-6 Decyltetradeceth-20, PPG-5 Ceteth-20, PPG-8 Ceteth-20, and PPG-23 Steareth-34.

It is most preferable that the polyoxyethylenated (1-40 EO) and polyoxypropylenated (1-30 PO) alkyl ($C_{16}$-$C_{30}$) ethers are (15-40 EO) and polyoxypropylenated (5-30 PO) alkyl ($C_{16}$-$C_{24}$) ethers, which could be selected from the group consisting of PPG-6 Decyltetradeceth-30, PPG-13 Decyltetradeceth-24, PPG-5 Ceteth-20, and PPG-8 Ceteth-20. They can also provide a composition with transparency for a long time.

As (7) silicone surfactants which can be used according to the present invention, mention may be made of those disclosed in documents U.S. Pat. Nos. 5,364,633 and 5,411,744.

The (7) silicone surfactant as the above nonionic surfactant may preferably be a compound of formula (I):

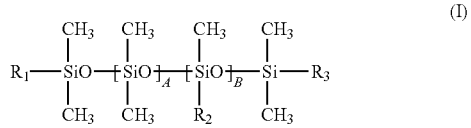

in which:
$R_1$, $R_2$ and $R_3$, independently of each other, represent a $C_1$-$C_6$ alkyl radical or a radical —$(CH_2)_x$—$(OCH_2CH_2)_y$—$(OCH_2CH_2)_z$—$OR_4$, at least one radical $R_1$, $R_2$ or $R_3$ not being an alkyl radical; $R_4$ being a hydrogen, an alkyl radical or an acyl radical;
A is an integer ranging from 0 to 200;
B is an integer ranging from 0 to 50; with the proviso that A and B are not simultaneously equal to zero;
x is an integer ranging from 1 to 6;
y is an integer ranging from 1 to 30;
z is an integer ranging from 0 to 5.

According to one preferred embodiment of the invention, in the compound of formula (I), the alkyl radical is a methyl radical, x is an integer ranging from 2 to 6 and y is an integer ranging from 4 to 30.

As examples of silicone surfactants of formula (I), mention may be made of the compounds of formula (II):

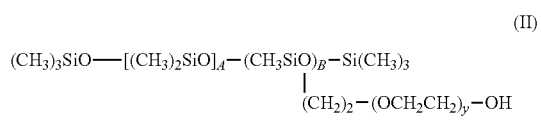

in which A is an integer ranging from 20 to 105, B is an integer ranging from 2 to 10 and y is an integer ranging from 10 to 20.

As examples of silicone surfactants of formula (I), mention may also be made of the compounds of formula (III):

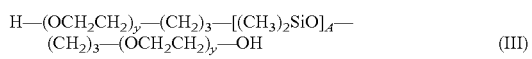

in which A' and y are integers ranging from 10 to 20.

Compounds of the invention which may be used are those sold by the company Dow Corning under the names DC 5329, DC 7439-146, DC 2-5695 and Q4-3667. The compounds DC 5329, DC 7439-146 and DC 2-5695 are compounds of formula (II) in which, respectively, A is 22, B is 2 and y is 12; A is 103, B is 10 and y is 12; A is 27, B is 3 and y is 12.

The compound Q4-3667 is a compound of formula (III) in which A is 15 and y is 13.

It is preferable that the (b) nonionic surfactant with an HLB value of from 8.0 to 14, preferably from 9.0 to 13.5, and more preferably from 10.0 to 13.0 be chosen from:
polyethylene glycol isostearate or oleate (8 to 10 mol of ethylene oxide),
polyethylene glycol isocetyl, behenyl ether or isostearyl ether (8 to 10 mol of ethylene oxide),
polyglyceryl monolaurate or dilaurate comprising 3 to 6 glycerol units,
polyglyceryl mono(iso)stearate comprising 3 to 6 glycerol units,
polyglyceryl monooleate comprising 3 to 6 glycerol units, and
polyglyceryl dioleate comprising 3 to 6 glycerol units.

According to a preferable embodiment of the present invention, the (b) nonionic surfactant with an HLB value of from 8.0 to 14, preferably from 9.0 to 13.5, and more preferably from 10.0 to 13.0, is selected from polyglyceryl fatty acid esters and mono- or poly-oxyalkylenated fatty acid esters.

It is preferable that the polyglyceryl fatty acid ester comprise esters of a fatty acid and polyglycerine containing 70% or more of polyglycerine whose polymerization degree is 4 or more, preferably esters of a fatty acid and polyglycerine containing equal to or more than 60% of polyglycerine whose polymerization degree is between 4 and 11, and more preferably esters of a fatty acid and polyglycerine containing equal to or more than 30% of polyglycerine whose polymerization degree is 5.

The polyglyceryl fatty acid ester may be chosen from the mono, di and tri esters of saturated or unsaturated acid, preferably saturated acid, including 2 to 30 carbon atoms, preferably 6 to 30 carbon atoms, and more preferably 8 to 30 carbon atoms, such as lauric acid, oleic acid, stearic acid, isostearic acid, capric acid, caprylic acid, and myristic acid.

It is preferable that the polyglyceryl fatty acid ester be selected from the group consisting of polyglyceryl (PG)-4 laurate, PG-5 laurate, PG5 dilaurate, PG-5 oleate, PG-5 dioleate, PG-6 tricaprylate, PG-5 myristate, PG-5 trimyristate, PG-5 stearate, PG-5 isostearate, PG-5 trioleate, PG-6 caprylate, and PG-6 tricaprylate.

It is preferable that the mono- or poly-oxyalkylenated fatty acid ester have a (poly)oxyalkylene moiety derived from 1 to 20 oxyalkylenes, preferably from 3 to 15 oxyalkylenes, and more preferably 8 to 10 oxyalkylenes.

The oxyalkylene moiety may be derived from alkylene glycols such as ethyleneglycol, propylene glycol, butyleneglycol, pentyleneglycol, hexyleneglycol, and the like. The oxyalkylene moiety may contain a number of moles of ethylene oxide and/or of propylene oxide of between 1 and 100 and preferably between 2 and 50. Advantageously, the nonionic surfactants do not comprise any oxypropylene units.

The mono- or poly-oxyalkylenated fatty acid ester may be chosen from the mono and di esters of saturated or unsaturated acid, preferably saturated acid, including 2 to 30 carbon atoms, preferably 6 to 30 carbon atoms, and more preferably 8 to 30 carbon atoms, such as lauric acid, oleic acid, stearic acid, isostearic acid, capric acid, caprylic acid, and myristic acid.

Examples of mono- or poly-oxyalkylenated fatty acid esters that may be mentioned include esters of saturated or unsaturated, linear or branched, $C_2$-$C_{30}$, preferably $C_6$-$C_{30}$ and more preferably $C_8$-$C_{22}$ acids and of polyethylene glycols.

Examples of mono- or poly-oxyalkylenated fatty acid esters that may be mentioned include the adducts of ethylene oxide with esters of lauric acid, myristic acid, palmitic acid, stearic acid, isostearic acid, oleic acid or behenic acid, and mixtures thereof, especially those containing from 8 to 20 oxyethylene groups, such as PEG-8 to PEG-20 laurate (as the CTFA names: PEG-8 laurate to PEG-20 laurate); PEG-8 to PEG-20 myristate (as the CTFA names: PEG-8 mysistate to PEG-20 mysistate); PEG-8 to PEG-20 palmitate (as the CTFA names: PEG-8 palmitate to PEG-20 palmitate); PEG-8 to PEG-20 stearate (as the CTFA names: PEG-8 stearate to PEG-20 stearate); PEG-8 to PEG-20 isostearate (as the CTFA names: PEG-8 isostearate to PEG-20 isostearate); PEG-8 to PEG-20 oleate (as the CTFA names: PEG-8 oleate to PEG-20 oleate); PEG-8 to PEG-20 behenate (as the CTFA names: PEG-8 behenate to PEG-20 behenate); and mixtures thereof.

It is preferable that polyglycol fatty acid ester be selected from the group consisting of PEG-8 isostearate, PEG-8 stearate, PEG-10 isostearate, PEG-10 oleate, PEG-10 isocetyl ether, PEG-10 behenyl ether or PEG-10 isostearyl ether and a mixture thereof.

Preferred nonionic surfactants are polyglyceryl fatty acid esters.

The amount in the composition according to the present invention of the (b) nonionic surfactant with an HLB value of from 8.0 to 14, preferably from 9.0 to 13.5, and more preferably from 10.0 to 13.0, is not limited, and may range from 0.1 to 30% by weight, preferably from 0.5 to 20% by weight, and more preferably from 1 to 10% by weight, relative to the total weight of the composition.

The weight ratio of the (b) nonionic surfactant to the (a) oil may be 2 or less, preferably from 1.5 or less, and more preferably from 1.0 or less.

(Ceramide Compound)

The composition according to the present invention comprises at least one ceramide compound. A single type of ceramide compound may be used, but two or more different types of ceramide compound may be used in combination.

According to the present invention, the term "ceramide compound" is understood to mean natural or synthetic ceramides and/or glycoceramides and/or pseudoceramides and/or neoceramides.

Ceramide compounds are disclosed, for example, in Patent Applications DE 4424530, DE 4424533, DE 4402929, DE 4420736, WO 95/23807, WO 94/07844, EP-A-0 646 572, WO 95/16665, FR-2 673 179, EP-A-0 227 994, WO 94/07844, WO 94/24097 and WO 94/10131, the teachings of which are included here by way of reference.

Ceramide compounds which can be used according to the present invention include, and in fact preferably correspond to, the general formula (I):

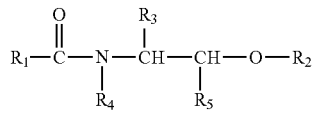

wherein
$R_1$ denotes:
either a saturated or unsaturated and linear or branched $C_1$-$C_{50}$, preferably $C_5$-$C_{50}$, hydrocarbon radical, it being possible for this radical to be substituted by one or more hydroxyl groups optionally esterified by an acid $R_7COOH$, $R_7$ being an optionally mono- or polyhydroxylated, saturated or unsaturated and linear or branched $C_1$-$C_{35}$ hydrocarbon radical, it being possible for the hydroxyl or hydroxyls of the $R_7$ radical to be esterified by an optionally mono- or polyhydroxylated, saturated or unsaturated and linear or branched $C_1$-$C_{35}$ fatty acid;
or an R"—(NR—CO)—R' radical, in which R denotes a hydrogen atom or a mono- or polyhydroxylated, preferably monohydroxylated, $C_1$-$C_{20}$ hydrocarbon radical, R' and R" are hydrocarbon radicals, the sum of the carbon atoms of which is between 9 and 30, R' being a divalent radical;
or an $R_8$—O—CO—$(CH_2)_p$ radical, in which $R_8$ denotes a $C_1$-$C_{20}$ hydrocarbon radical and p is an integer varying from 1 to 12;

$R_2$ is chosen from a hydrogen atom, a radical of saccharide type, in particular a $(glycosyl)_n$, $(galactosyl)_n$, or sulphogalactosyl radical, a sulphate or phosphate residue, a phosphorylethylamine radical and a phosphorylethylammonium radical, in which n is an integer varying from 1 to 4 and m is an integer varying from 1 to 8;

$R_3$ denotes a hydrogen atom or a hydroxylated or nonhydroxylated and saturated or unsaturated $C_1$-$C_{33}$ hydrocarbon radical, it being possible for the hydroxyl or hydroxyls to be esterified by an inorganic acid or an acid $R_7COOH$, $R_7$ having the same meanings as hereinabove, and it being possible for the hydroxyl or hydroxyls to be etherified by a $(glycosyl)_n$, $(galactosyl)_m$, sulphogalactosyl, phosphorylethylamine or phosphorylethylammonium radical, in which n is an integer varying from 1 to 4 and m is an integer varying from 1 to 8, it also being possible for $R_3$ to be substituted by one or more $C_1$-$C_{14}$ alkyl radicals;

$R_4$ denotes a hydrogen atom, a methyl or ethyl radical, an optionally hydroxylated, saturated or unsaturated and linear or branched $C_3$-$C_{50}$ hydrocarbon radical or a —$CH_2$—CHOH—$CH_2$—O—$R_6$ radical, in which $R_6$ denotes a $C_{10}$-$C_{26}$ hydrocarbon radical, or an $R_8$—O—CO—$(CH_2)_p$ radical, in which $R_8$ denotes a $C_1$-$C_{20}$ hydrocarbon radical and p is an integer varying from 1 to 12;

$R_5$ denotes a hydrogen atom or an optionally mono- or polyhydroxylated, saturated or unsaturated and linear or branched $C_1$-$C_{30}$ hydrocarbon radical, it being possible for the hydroxyl or hydroxyls to be etherified by a $(glycosyl)_n$, $(galactosyl)_m$, sulphogalactosyl, phosphorylethylamine or phosphorylethylammonium radical, in which n is an integer varying from 1 to 4 and m is an integer varying from 1 to 8;
with the proviso that, when $R_3$ and $R_5$ denote hydrogen or when $R_3$ denotes hydrogen and $R_5$ denotes methyl, then $R_4$ does not denote a hydrogen atom or a methyl or ethyl radical.

Preference is given, among the compounds of formula (I), to the ceramides and/or glycoceramides with the structure described by Downing in Journal of Lipid Research, Vol. 35, 2060-2068, 1994, or those disclosed in French Patent Application FR-2 673 179, the teachings of which are incorporated herein by reference.

It is preferable that, in the above formula (I), $R_3$ denote a $C_{15}$-$C_{26}$ α-hydroxyalkyl radical, the hydroxyl group optionally being esterified by a $C_{16}$-$C_{30}$ α-hydroxy acid.

The ceramide compounds which are more particularly preferred according to the invention are the compounds of formula (I) for which $R_1$ denotes an optionally hydroxylated and saturated or unsaturated alkyl derived from $C_{14}$-$C_{22}$ fatty acids; $R_2$ denotes a hydrogen atom; and $R_3$ denotes an optionally hydroxylated and linear $C_{11}$-$C_{17}$ radical and preferably $C_{13}$-$C_{15}$ radical. $R_3$ preferably denotes an α-hydroxycetyl radical and $R_2$, $R_4$ and $R_5$ denote a hydrogen atom.

It is preferable that the (c) ceramide compound be selected from the group consisting of 2-N-linoleoylaminooctadecane-1,3-diol, 2-N-oleoylaminooctadecane-1,3-diol, 2-N-palmitoylaminooctadecane-1,3-diol, 2-N-stearoylaminooctadecane-1,3-diol, 2-N-behenoylaminooctadecane-1,3-diol, 2-N-[2-hydroxypalmitoyl]aminooctadecane-1,3-diol, 2-N-stearoylaminooctadecane-1,3,4-triol, 2-N-palmitoylaminohexadecane-1,3-diol, and mixtures thereof.

It is also preferable that the (c) ceramide compound be chosen from bis(N-hydroxyethyl-N-cetyl)malonamide, the N-(2-hydroxyethyl)-N-(3-cetyloxy-2-hydroxypropyl)amide of cetylic acid and N-docosanoyl-N-methyl-D-glucamine.

Use may also be made of mixtures of ceramide compounds, such as, for example, the mixtures of ceramide(s) 2 and ceramide(s) 5 according to the Downing classification.

Particular use may also be made of the compounds of formula (I) for which $R_1$ denotes a saturated or unsaturated alkyl radical derived from $C_{12}$-$C_{22}$ fatty acids; $R_2$ denotes a galactosyl or sulphogalactosyl radical; and $R_3$ denotes a saturated or unsaturated $C_{12}$-$C_{22}$ hydrocarbon radical and preferably a —CH=CH—$(CH_2)_{12}$—$CH_3$ group.

Mention may be made, by way of example, of the product composed of a mixture of glycoceramides sold under the trade name Glycocer by Waitaki International Biosciences.

Use may also be made of the compounds of formula (I) disclosed in Patent Applications EP-A-0 227 994, EP-A-0 647 617, EP-A-0 736 522 and WO 94/07844.

Such compounds include, for example, Questamide H (bis(N-hydroxyethyl-N-cetyl)malonamide), sold by Quest, or the N-(2-hydroxyethyl)-N-(3-cetyloxy-2-hydroxy-propyl)amide of cetylic acid.

Use may also be made of N-docosanoyl-N-methyl-D-glucamine, disclosed in Patent Application WO 94/24097.

It is of course possible to use mixtures of the various ceramide compounds in the invention compositions.

The amount of the (c) ceramide compound may range from 0.01 to 20% by weight, preferably from 0.1 to 15% by weight, and more preferably from 0.1 to 10% by weight, relative to the total weight of the composition.

The weight ratio of the (b) nonionic surfactant to the (c) ceramide compound may be 15 or less, preferably 10 or less, and more preferably from 6 or less.

(Anionic Surfactant)

The composition according to the present invention comprises at least one (d) anionic surfactant. A single type of (d) anionic surfactant may be used, but two or more different types of (d) anionic surfactant may be used in combination.

The (d) anionic surfactant is not limited. The (d) anionic surfactants may be chosen in particular from anionic derivatives of proteins of vegetable origin or of silk proteins, phosphates and alkyl phosphates, carboxylates, sulphosuccinates, amino acid derivatives, alkyl sulphates, alkyl ether sulphates, sulphonates, isethionates, taurates, alkyl sulphoacetates, polypeptides, anionic derivatives of alkyl polyglucosides, and their mixtures.

1) Anionic derivatives of proteins of vegetable origin are protein hydrolysates comprising a hydrophobic group, it being possible for the said hydrophobic group to be naturally present in the protein or to be added by reaction of the protein and/or of the protein hydrolysate with a hydrophobic compound. The proteins are of vegetable origin or derived from silk, and the hydrophobic group can in particular be a fatty chain, for example an alkyl chain comprising from 10 to 22 carbon atoms. Mention may more particularly be made, as anionic derivatives of proteins of vegetable origin, of apple, wheat, soybean or oat protein hydrolysates comprising an alkyl chain having from 10 to 22 carbon atoms, and their salts. The alkyl chain can in particular be a lauryl chain and the salt can be a sodium, potassium and/or ammonium salt.

Thus, mention may be made, as protein hydrolysates comprising a hydrophobic group, for example, of salts of protein hydrolysates where the protein is a silk protein modified by lauric acid, such as the product sold under the name Kawa Silk by Kawaken; salts of protein hydrolysates where the protein is a wheat protein modified by lauric acid, such as the potassium salt sold under the name Aminofoam W OR by Croda (CTFA name: potassium lauroyl wheat amino acids) and the sodium salt sold under the name Proteol LW 30 by Seppic (CTFA name: sodium lauroyl wheat amino acids); salts of protein hydrolysates where the protein is an oat protein comprising an alkyl chain having from 10 to 22 carbon atoms and more especially salts of protein hydrolysates where the protein is an oat protein modified by lauric acid, such as the sodium salt sold under the name Proteol OAT (30% aqueous solution) by Seppic (CTFA name: sodium lauroyl oat amino acids); or salts of apple protein hydrolysates comprising an alkyl chain having from 10 to 22 carbon atoms, such as the sodium salt sold under the name Proteol APL (30% aqueous/glycol solution) by Seppic (CTFA name: sodium cocoyl apple amino acids). Mention may also be made of the mixture of lauroyl amino acids (aspartic acid, glutamic acid, glycine, alanine) neutralized with sodium N-methylglycinate sold under the name Proteol SAV 50 S by Seppic (CTFA name: sodium cocoyl amino acids).

2) Mention may be made, as phosphates and alkyl phosphates, for example, of monoalkyl phosphates and dialkyl phosphates, such as lauryl monophosphate, sold under the name MAP 20® by Kao Chemicals, the potassium salt of dodecyl phosphate, the mixture of mono- and diesters (predominantly diester) sold under the name Crafol AP-31® by Cognis, the mixture of octyl phosphate monoester and diester, sold under the name Crafol AP-20® by Cognis, the mixture of ethoxylated (7 mol of EO) 2-butyloctyl phosphate monoester and diester, sold under the name Isofol 12 7 EO-Phosphate Ester® by Condea, the potassium or triethanolamine salt of mono($C_{12}$-$C_{13}$)alkyl phosphate, sold under the references Arlatone MAP 230K-40® and Arlatone MAP 230T-60® by Uniqema, potassium lauryl phosphate, sold under the name Dermalcare MAP XC-99/09® by Rhodia Chimie, and potassium cetyl phosphate, sold under the name Arlatone MAP 160K by Uniqema.

3) Mention may be made, as carboxylates, of:
  amido ether carboxylates (AEC), such as sodium lauryl amido ether carboxylate (3 EO), sold under the name Akypo Foam 30® by Kao Chemicals;
  polyoxyethylenated carboxylic acid salts, such as oxyethylenated (6 EO) sodium lauryl ether carboxylate (65/25/10 $C_{12}$-$C_{14}$-$C_{16}$), sold under the name Akypo Soft 45 NV® by Kao Chemicals, polyoxyethylenated and carboxymethylated fatty acids originating from olive oil, sold under the name Olivem 400® by Biologia E Tecnologia, or oxyethylenated (6 EO) sodium tridecyl ether carboxylate, sold under the name Nikkol ECTD-6NEX® by Nikkol; and
  salts of fatty acids (soaps) having a $C_6$ to $C_{22}$ alkyl chain which are neutralized with an organic or inorganic base, such as potassium hydroxide, sodium hydroxide, triethanolamine, N-methylglucamine, lysine and arginine.

4) Mention may in particular be made, as amino acid derivatives, of alkali salts of amino acids, such as:
  sarcosinates, such as sodium lauroyl sarcosinate, sold under the name Sarkosyl NL 97® by Ciba or sold under the name Oramix L 30® by Seppic, sodium myristoyl sarcosinate, sold under the name Nikkol Sarcosinate MN® by Nikkol, or sodium palmitoyl sarcosinate, sold under the name Nikkol Sarcosinate PN® by Nikkol;
  alaninates, such as sodium N-lauroyl-N-methylamidopropionate, sold under the name Sodium Nikkol Alaninate LN 30® by Nikkol or sold under the name Alanone ALE® by Kawaken, or triethanolamine N-lauroyl-N-methylalanine, sold under the name Alanone ALTA® by Kawaken;

glutamates, such as triethanolamine monococoyl glutamate, sold under the name Acylglutamate CT-12S by Ajinomoto, triethanolamine lauroyl glutamate, sold under the name Acylglutamate LT-128 by Ajinomoto;

aspartates, such as the mixture of triethanolamine N-lauroyl aspartate and triethanolamine N-myristoyl aspartate, sold under the name Asparack® by Mitsubishi;

glycine derivatives (glycinates), such as sodium N-cocoyl glycinate, sold under the names Amilite GCS-12® and Amilite GCK 12 by Ajinomoto;

citrates, such as the citric monoester of oxyethylenated (9 mol) coco alcohols, sold under the name Witconol EC 1129 by Goldschmidt; and galacturonates, such as sodium dodecyl D-galactoside uronate, sold by Soliance.

5) Mention may be made, as sulphosuccinates, for example, of oxyethylenated (3 EO) lauryl (70/30 $C_{12}/C_{14}$) alcohol monosulphosuccinate, sold under the names Setacin 103 Special® and Rewopol SB-FA 30 K 4® by Witco, the disodium salt of a hemisulphosuccinate of $C_{12}$-$C_{14}$ alcohols, sold under the name Setacin F Special Paste® by Zschimmer Schwarz, oxyethylenated (2 EO) disodium oleamidosulphosuccinate, sold under the name Standapol SH 135® by Cognis, oxyethylenated (5 EO) lauramide monosulphosuccinate, sold under the name Lebon A-5000® by Sanyo, the disodium salt of oxyethylenated (10 EO) lauryl citrate monosulphosuccinate, sold under the name Rewopol SB CS 50® by Witco, or ricinoleic monoethanolamide monosulphosuccinate, sold under the name Rewoderm S 1333® by Witco. Use may also be made of polydimethylsiloxane sulphosuccinates, such as disodium PEG-12 dimethicone sulphosuccinate, sold under the name Mackanate-DC 30 by MacIntyre.

6) Mention may be made, as alkyl sulphates, for example, of triethanolamine lauryl sulphate (CTFA name: TEA lauryl sulphate), such as the product sold by Huntsman under the name Empicol TL40 FL or the product sold by Cognis under the name Texapon T42, which products are at 40% in aqueous solution. Mention may also be made of ammonium lauryl sulphate (CTFA name: ammonium lauryl sulphate), such as the product sold by Huntsman under the name Empicol AL 30FL, which is at 30% in aqueous solution.

7) Mention may be made, as alkyl ether sulphates, for example, of sodium lauryl ether sulphate (CTFA name: sodium laureth sulphate), such as that sold under the names Texapon N40 and Texapon AOS 225 UP by Cognis, or ammonium lauryl ether sulphate (CTFA name: ammonium laureth sulphate), such as that sold under the name Standapol EA-2 by Cognis.

8) Mention may be made, as sulphonates, for example, of α-olefinsulphonates, such as sodium α-olefinsulphonate ($C_{14}$-$C_{16}$), sold under the name Bio-Terge AS-40® by Stepan, sold under the names Witconate AOS Protégé® and Sulframine AOS PH 12® by Witco or sold under the name Bio-Terge AS-40 CG® by Stepan, secondary sodium olefinsulphonate, sold under the name Hostapur SAS 30® by Clariant; or linear alkylarylsulphonates, such as sodium xylenesulphonate, sold under the names Manrosol SXS30®, Manrosol SXS40® and Manrosol SXS93® by Manro.

9) Mention may be made, as isethionates, of acylisethionates, such as sodium cocoylisethionate, such as the product sold under the name Jordapon CI P® by Jordan.

10) Mention may be made, as taurates, of the sodium salt of palm kernel oil methyltaurate, sold under the name Hostapon CT Paté® by Clariant; N-acyl-N-methyltaurates, such as sodium N-cocoyl-N-methyltaurate, sold under the name Hostapon LT-SF® by Clariant or sold under the name Nikkol CMT-30-T® by Nikkol, sodium palmitoyl methyltaurate, sold under the name Nikkol PMT® by Nikkol, or sodium steraroyl methyltaurate, sold under the name Sunsoft O-30S by Taiyo Kagaku.

11) The anionic derivatives of alkyl polyglucosides can in particular be citrates, tartrates, sulphosuccinates, carbonates and glycerol ethers obtained from alkyl polyglucosides. Mention may be made, for example, of the sodium salt of cocoylpolyglucoside (1,4) tartaric ester, sold under the name Eucarol AGE-ET® by Cesalpinia, the disodium salt of cocoylpolyglucoside (1,4) sulphosuccinic ester, sold under the name Essai 512 MP® by Seppic, or the sodium salt of cocoylpolyglucoside (1,4) citric ester, sold under the name Eucarol AGE-EC® by Cesalpinia.

It is preferable that the (d) anionic surfactant be selected from taurate or glutamate, more preferably N-acyl-N-methyltaurate, and even more preferably sodium N-stearoyl-N-methyl-taurate.

It is preferable that the amino acid derivatives be acyl glycine derivatives or glycine derivatives, in particular acyl glycine salt.

The acyl glycine derivatives or glycine derivatives can be chosen from acyl glycine salts (or acyl glycinates) or glycine salts (or glycinates), and in particular from the following.

i) Acyl glycinates of formula (I):

R—HNCH$_2$COOX    (I)

in which

R represents an acyl group R'C=O, with R', which represents a saturated or unsaturated, linear or branched, hydrocarbon chain, preferably comprising from 10 to 30 carbon atoms, preferably from 12 to 22 carbon atoms, preferably from 14 to 22 carbon atoms and better still from 16 to 20 carbon atoms, and X represents a cation chosen, for example, from the ions of alkali metals, such as Na, Li or K, preferably Na or K, the ions of alkaline earth metals, such as Mg, ammonium groups and their mixtures.

The acyl group can in particular be chosen from the lauroyl, myristoyl, behenoyl, palmitoyl, stearoyl, isostearoyl, olivoyl, cocoyl or oleoyl groups and their mixtures.

Preferably, R is a cocoyl group.

ii) Glycinates of following formula (II):

in which:

R$_1$ represents a saturated or unsaturated, linear or branched, hydrocarbon chain comprising from 10 to 30 carbon atoms, preferably from 12 to 22 carbon atoms and better still from 16 to 20 carbon atoms; R$_1$ is advantageously chosen from the lauryl, myristyl, palmityl, stearyl, cetyl, cetearyl or oleyl groups and their mixtures and preferably from the stearyl and oleyl groups, the R$_2$ groups, which are identical or different, represent an R"OH group, R" being an alkyl group comprising from 2 to 10 carbon atoms, preferably from 2 to 5 carbon atoms.

Mention may be made, as compound of formula (I), for example, of the compounds carrying the INCI name sodium cocoyl glycinate, such as, for example, Amilite GCS-12, sold by Ajinomoto, or potassium cocoyl glycinate, such as, for example, Amilite GCK-12 from Ajinomoto.

Use may be made, as compounds of formula (II), of dihydroxyethyl oleyl glycinate or dihydroxyethyl stearyl glycinate.

The amount of the (d) anionic surfactant may range from 0.01 to 20% by weight, preferably from 0.05 to 10% by weight, and more preferably from 0.1 to 5% by weight, relative to the total weight of the composition.

(Water)

The composition according to the present invention comprises water.

The amount of water is not limited, and may be from 40 to 90% by weight, preferably from 50 to 85% by weight, and more preferably from 60 to 80% by weight, relative to the total weight of the composition.

(Additional Surfactant)

The composition according to the present invention may further comprise at least one nonionic surfactant different from the above (b) and/or at least one additional ionic surfactant. A single type of additional surfactant may be used, but two or more different types of additional surfactant may be used in combination.

As the additional surfactant, at least one nonionic surfactant with an HLB value less than 8.0 or more than 14 may be used.

As the additional nonionic surfactant, mention may be made of those listed for the above (b) except that the additional nonionic surfactant has an HLB value less than 8.0, preferably less than 9.0, and more preferably less than 10.0, and more than 14, preferably more than 13.5, and more preferably more than 13.0.

As the additional surfactant(s), cationic surfactants and/or amphoteric surfactants may be used.

(Cationic Surfactant)

The cationic surfactant is not limited. The cationic surfactant may be selected from the group consisting of optionally polyoxyalkylenated, primary, secondary or tertiary fatty amine salts, quaternary ammonium salts, and mixtures thereof.

Examples of quaternary ammonium salts that may be mentioned include, but are not limited to:
those of general formula (I) below:

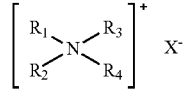 (I)

wherein
$R_1$, $R_2$, $R_3$, and $R_4$, which may be identical or different, are chosen from linear and branched aliphatic radicals comprising from 1 to 30 carbon atoms and optionally comprising heteroatoms such as oxygen, nitrogen, sulfur and halogens. The aliphatic radicals may be chosen, for example, from alkyl, alkoxy, $C_2$-$C_6$ polyoxyalkylene, alkylamide, ($C_{12}$-$C_{22}$)alkylamido($C_2$-$C_6$)alkyl, ($C_{12}$-$C_{22}$)alkylacetate and hydroxyalkyl radicals; and aromatic radicals such as aryl and alkylaryl; and X" is chosen from halides, phosphates, acetates, lactates, ($C_2$-$C_6$) alkyl sulfates and alkyl- or alkylaryl-sulfonates;
quaternary ammonium salts of imidazoline;
diquaternary ammonium salts; and
quaternary ammonium salts comprising at least one ester function.

Among the quaternary ammonium salts mentioned above that may be used in compositions according to the invention include, but are not limited to tetraalkylammonium chlorides, for instance dialkyldimethylammonium and alkyltrimethylammonium chlorides in which the alkyl radical comprises from about 12 to 22 carbon atoms, such as behenyltrimethylammonium, distearyldimethylammonium, cetyltrimethylammonium and benzyldimethylstearylammonium chloride; palmitylamidopropyltrimethylammonium chloride; and stearamidopropyldimethyl(myristyl acetate) ammonium chloride, sold under the name "Ceraphyl® 70" by the company Van Dyk.

According to one embodiment, the cationic surfactant that may be used in the compositions of the invention is chosen from quaternary ammonium salts, for example from behenyltrimethylammonium chloride, cetyltrimethylammonium chloride, Quaternium-83, Quaternium-87, Quaternium-22, behenylamidopropyl-2,3-dihydroxypropyldimethylammonium chloride, palmitylamidopropyltrimethylammonium chloride, and stearamidopropyldimethylamine.

(Amphoteric Surfactant)

The amphoteric surfactant is not limited. The amphoteric or zwitterionic surfactants can be, for example (nonlimiting list), amine derivatives such as aliphatic secondary or tertiary amine, and optionally quaternized amine derivatives, in which the aliphatic radical is a linear or branched chain comprising 8 to 22 carbon atoms and containing at least one water-solubilizing anionic group (for example, carboxylate, sulphonate, sulphate, phosphate or phosphonate).

Among the amidoaminecarboxylated derivatives, mention may be made of the products sold under the name Miranol, as described in U.S. Pat. Nos. 2,528,378 and 2,781,354 and classified in the CTFA dictionary, 3rd edition, 1982 (the disclosures of which are incorporated herein by reference), under the names Amphocarboxyglycinates and Amphocarboxypropionates, with the respective structures:

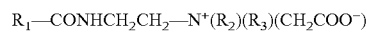

in which:
$R_1$ denotes an alkyl radical of an acid $R_1$—COOH present in hydrolysed coconut oil, a heptyl, nonyl or undecyl radical,
$R_2$ denotes a beta-hydroxyethyl group, and
$R_3$ denotes a carboxymethyl group; and

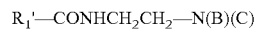

in which:
B represents —$CH_2CH_2OX'$,
C represents —$(CH_2)_z Y'$, with z=1 or 2,
X' denotes a —$CH_2CH_2$—COOH group, —$CH_2$—COOZ',
—$CH_2CH_2$—COOH, —$CH_2CH_2$—COOZ' or a hydrogen atom,
Y' denotes —COOH, —COOZ', —$CH_2$—CHOH—$SO_3Z'$ or a —$CH_2$—CHOH—$SO_3H$ radical,
Z' represents an ion of an alkaline or alkaline earth metal such as sodium, an ammonium ion or an ion issued from an organic amine, and
$R_1$' denotes an alkyl radical of an acid $R_1$'—COOH present in coconut oil or in hydrolysed linseed oil, an alkyl radical, such as a $C_7$, $C_9$, $C_{11}$ or $C_{13}$ alkyl radical, a $C_{17}$ alkyl radical and its iso form, or an unsaturated $C_{17}$ radical.

It is preferable that the amphoteric surfactant be selected from ($C_8$-$C_{24}$)-alkyl amphomonoacetates, ($C_8$-$C_{24}$)alkyl amphodiacetates, ($C_8$-$C_{24}$)alkyl amphomonopropionates, and ($C_8$-$C_{24}$)alkyl amphodipropionates.

These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphopropionate, Disodium Caprylamphodipropionate, Disodium Caprylamphodipropionate, Lauroamphodipropionic acid and Cocoamphodipropionic acid.

By way of example, mention may be made of the cocoamphodiacetate sold under the trade name Miranol® C2M concentrate by the company Rhodia Chimie.

Preferably, the amphoteric surfactant may be a betaine.

The betaine-type amphoteric surfactant is preferably selected from the group consisting of alkylbetaines, alkylamidoalkylbetaines, alkylsulfobetaines, alkylphosphobetaines, and alkylamidoalkylsulfobetaines, in particular, $(C_8-C_{24})$alkylbetaines, $(C_8-C_{24})$alkylamido$(C_1-C_8)$alkylbetaines, $(C_8-C_{24})$alkylsulphobetaines, and $(C_8-C_{24})$alkylamido$(C_1-C_8)$alkylsulphobetaines. In one embodiment, the amphoteric surfactants of betaine type are chosen from $(C_8-C_{24})$alkylbetaines, $(C_8-C_{24})$alkylamido$(C_1-C_8)$alkylsulphobetaines, $(C_8-C_{24})$alkylsulphobetaines, and alkyl$(C_8-C_{24})$phosphobetaines.

Non-limiting examples that may be mentioned include the compounds classified in the CTFA dictionary, 9th edition, 2002, under the names cocobetaine, laurylbetaine, cetylbetaine, coco/oleamidopropylbetaine, cocamido propyl betaine, palmitamido propylbetaine, stearamidopropylbetaine, cocamidoethylbetaine, cocamidopropylhydroxysultaine, oleamidopropylhydroxysultaine, cocohydroxysultaine, laurylhydroxysultaine, and cocosultaine, alone or as mixtures.

The betaine-type amphoteric surfactant is preferably an alkylbetaine and an alkylamidoalkylbetaine, in particular cocobetaine and cocamidopropylbetaine.

The amount of the additional surfactant(s) may be from 0.01 to 20% by weight, preferably from 0.10 to 10% by weight, and more preferably from 1 to 5% by weight, relative to the total weight of the composition.

(Polyol)

The composition according to the present invention may further comprise at least one polyol. A single type of polyol may be used, but two or more different types of polyol may be used in combination.

The term "polyol" here means an alcohol having two or more hydroxy groups, and does not encompass a saccharide or a derivative thereof. The derivative of a saccharide includes a sugar alcohol which is obtained by reducing one or more carbonyl groups of a saccharide, as well as a saccharide or a sugar alcohol in which the hydrogen atom or atoms in one or more hydroxy groups thereof has or have been replaced with at least one substituent such as an alkyl group, a hydroxyalkyl group, an alkoxy group, an acylgroup or a carbonyl group.

The polyol may be a $C_2-C_{12}$ polyol, preferably a $C_{2-9}$ polyol, comprising at least 2 hydroxy groups, and preferably 2 to 5 hydroxy groups.

The polyol may be a natural or synthetic polyol. The polyol may have a linear, branched or cyclic molecular structure.

The polyol may be selected from glycerins and derivatives thereof, and glycols and derivatives thereof. The polyol may be selected from the group consisting of glycerin, diglycerin, polyglycerin, ethyleneglycol, propyleneglycol, dipropyleneglycol, butyleneglycol, pentyleneglycol, hexyleneglycol, 1,3-propanediol, 1,5-pentanediol, polyethyleneglycol (5 to 50 ethyleneoxide groups), and sugars such as sorbitol.

The polyol may be present in an amount ranging from 0.01 to 30% by weight, and preferably from 0.1 to 20% by weight, such as from 1 to 10% by weight, relative to the total weight of the composition.

(Thickening Agent)

The composition according to the present invention may further comprise at least one thickening agent. A single type of thickening agent may be used, but two or more different types of thickening agent may be used in combination.

The thickening agent may be selected from organic and inorganic thickeners.

The organic thickeners may be chosen at least one of:
(i) associative thickeners;
(ii) crosslinked acrylic acid homopolymers;
(iii) crosslinked copolymers of (meth)acrylic acid and of $(C_1-C_6)$alkyl acrylate;
(iv) nonionic homopolymers and copolymers comprising at least one of ethylenically unsaturated ester monomers and ethylenically unsaturated amide monomers;
(v) ammonium acrylate homopolymers and copolymers of ammonium acrylate and of acrylamide;
(vi) polysaccharides; and
(vii) $C_{12}-C_{30}$ fatty alcohols.

The thickening agent is preferably selected from associative thickeners and polysaccharides such as starch and xanthan gum.

As used herein, the expression "associative thickener" means an amphiphilic thickener comprising both hydrophilic units and hydrophobic units, for example, comprising at least one $C_8-C_{30}$ fatty chain and at least one hydrophilic unit.

The viscosity of the composition according to the present invention is not particularly limited. The viscosity can be measured at 25° C. with viscosimeters or rheometers preferably with coneplan geometry. Preferably, the viscosity of the composition according to the present invention can range, for example, from 1 to 2000 Pa·s, and preferably from 1 to 1000 Pa·s at 25° C. and 1 s$^{-1}$.

The thickening agent may be present in an amount ranging from 0.001 to 10% by weight, and preferably from 0.01 to 10% by weight, such as from 0.1 to 5% by weight, relative to the total weight of the composition.

(Other Ingredients)

The composition according to the present invention may also comprise an effective amount of other ingredients, known previously elsewhere compositions, such as various common adjuvants, antiageing agents, whitening agents, anti-greasy skin agents, sequestering agents such as EDTA and etidronic acid, UV screening agents, preserving agents, vitamins or provitamins, for instance, panthenol, opacifiers, fragrances, plant extracts, cationic polymers and so on.

The composition according to the present invention may further comprise at least one organic solvent. So the organic solvent is preferably water miscible. As the organic solvent, there may be mentioned, for example, $C_1-C_4$ alkanols, such as ethanol and isopropanol; aromatic alcohols such as benzyl alcohol and phenoxyethanol; analogous products; and mixtures thereof.

The organic water-soluble solvents may be present in an amount ranging from less than 10% by weight, preferably from 5% by weight or less, and more preferably from 1% by weight or less, relative to the total weight of the composition.

[Preparation and Properties]

The composition according to the present invention can be prepared by mixing the above essential and optional ingredients in accordance with a conventional process. The conventional process includes mixing with a high pressure homogenizer (a high energy process). Alternatively, the composition can be prepared by a low energy processes such as phase inversion temperature process (PIT), phase inversion concentration (PIC), autoemulsification, and the like. Preferably, the composition is prepared by a low energy process.

The weight ratio of the (b) nonionic surfactant to the (a) oil may be from 0.01 to 2, preferably from 0.1 to 1.5, and more preferably from 0.5 to 1.0. In particular, the weight ratio of the (b) nonionic surfactant/the (a) oil may be 1 or less, such as from 0.5 to 1.0, preferably from 0.4 to 0.9, and more preferably from 0.3 to 0.8.

The composition according to the present invention is in the form of a nano- or micro-emulsion.

The "micro-emulsion" may be defined in two ways, namely, in a broader sense and in a narrower sense. That is to say, there are one case ("microemulsion in the narrow sense") in which the microemulsion refers to a thermodynamically stable isotropic single liquid phase containing a ternary system having three ingredients of an oily component, an aqueous component and a surfactant, and the other case ("micro-emulsion in the broad sense") in which among thermodynamically unstable typical emulsion systems the microemulsion additionally includes those such emulsions presenting transparent or translucent appearances due to their smaller particle sizes (Satoshi Tomomasa, et al., OilChemistry, Vol. 37, No. 11 (1988), pp. 48-53). The "micro-emulsion" as used herein refers to a "micro-emulsion in the narrow sense," i.e., a thermodynamically stable isotropic single liquid phase.

The micro-emulsion refers to either one state of an O/W (oil-in-water) type microemulsion in which oil is solubilized by micelles, a W/O (water-in-oil) type microemulsion in which water is solubilized by reverse micelles, or a bicontinuous microemulsion in which the number of associations of surfactant molecules are rendered infinite so that both the aqueous phase and oil phase have a continuous structure.

The micro-emulsion may have a dispersed phase with a number average diameter of 100 nm or less, preferably 50 nm or less, and more preferably 20 nm or less, measured by laser granulometry.

The "nano-emulsion" here means an emulsion characterized by a dispersed phase with a size of less than 350 nm, the dispersed phase being stabilized by a crown of the (b) nonionic surfactant that may optionally form a liquid crystal phase of lamellar type, at the dispersed phase/continuous phase interface. In the absence of specific opacifiers, the transparency of the nano-emulsions arises from the small size of the dispersed phase, this small size being obtained by virtue of the use of mechanical energy and especially a high-pressure homogenizer.

Nano-emulsions can be distinguished from microemulsions by their structure. Specifically, micro-emulsions are thermodynamically stable dispersions formed from, for example, the (b) nonionic surfactant micells swollen with the (a) oil. Furthermore, microemulsions do not require substantial mechanical energy in order to be prepared.

The nano-emulsion may have a dispersed phase with a number average diameter of 300 nm or less, preferably 200 nm or less, and more preferably 100 nm or less, measured by laser granulometry.

The composition according to the present invention may be in the form of an O/W nano- or micro-emulsion, a W/O nano- or micro-emulsion or a bicontinuous emulsion. It is preferable that the composition according to the present invention be in the form of an O/W nano- or micro-emulsion.

It is preferable that the composition according to the present invention be in the form of an O/W emulsion. The (a) oil may be in the form of a droplet with a number average particle size of, preferably 300 nm or less, more preferably 200 nm or less, and more preferably from 100 nm or less.

The composition according to the present invention can have a transparent or slightly translucent appearance, preferably a transparent appearance.

Composition

The transparency may be determined by measuring the turbidity with, for example, a 2100Q (HACH) with a round cell (25 mm in diameter×60 mm height) and a tungsten filament lump.

The composition according to the present invention may have a turbidity of less than 300, and preferably 200 or less.

[Process and Use]

The composition according to the present invention can be used for a non-therapeutic process, such as a cosmetic process, for treating the skin, the hair, mucous membranes, the nails, the eyelashes, the eyebrows and/or the scalp, by being applied to the skin, the hair, mucous membranes, the nails, the eyelashes, the eyebrows or the scalp.

Thus, in one particular embodiment, the composition according to the invention is a cosmetic composition.

The present invention also relates to a use of the composition according to the present invention, as it is or in care products and/or washing products and/or make-up products and/or make-up-removing products, for body and/or facial skin and/or mucous membranes and/or the scalp and/or the hair and/or the nails and/or the eyelashes and/or the eyebrows.

In other words, the composition according to the present invention can be used, as it is, as the above product. Alternatively, the composition according to the present invention can be used as an element of the above product. For example the composition according to the present invention can be added to or combined with any other elements to form the above product.

The care product may be a lotion, a cream, a serum, a hair tonic, a hair conditioner, a sun screening agent, and the like. The washing product may be a shampoo, a face wash, a hand wash and the like. The make-up product may be a foundation, a mascara, a lipstick, a lip gloss, a blusher, an eye shadow, a nail varnish, and the like. The make-up-removing product may be a make-up cleansing agent and the like.

EXAMPLES

The present invention will be described in a more detailed manner by way of examples. However, these examples should not be construed as limiting the scope of the present invention.

Examples 1-2 and Comparative Examples 1-4

The following compositions according to Examples (Ex.) 1-2 and Comparative Examples (Comp.) 1-4, shown in Table 1, were prepared by mixing the components shown in Table 1 as follows:

(A) Examples 1 and 2

(1) mixing 2-oleamido-1,3-octanediol, ethylhexyl palmitate, and PG-5 laurate or PG-5 oleate to form an oil phase;
(2) heating the oil phase up to around 80° C.;
(3) mixing water, Na methyl stearoyl taurate, phenoxyethanol, chlorphenesin, and butyleneglycol, to form an aqueous phase;
(4) heating the aqueous phase up to around 80° C.;
(5) adding the aqueous phase into the oil phase followed by mixing them to obtain an O/W emulsion; and
(6) mixing xanthan gum, glycerin and water to the emulsion, followed by cooling the mixture down to room temperature.

(B) Comparative Example 1

(1) mixing 2-oleamido-1,3-octanediol, and ethylhexyl palmitate to form an oil phase;
(2) heating the oil phase up to around 80° C.;
(3) mixing water, Na methyl stearoyl taurate, phenoxyethanol, chlorphenesin, butyleneglycol, to form an aqueous phase;
(4) heating the aqueous phase up to around 80° C.;
(5) adding the aqueous phase into the oil phase followed by mixing them to obtain an O/W emulsion; and
(6) mixing xanthan gum, glycerin and water to the emulsion, followed by cooling the mixture down to room temperature.

(C) Comparative Example 2

(1) mixing 2-oleamido-1,3-octanediol, ethylhexyl palmitate, and PG-5 laurate to form an oil phase;
(2) heating the oil phase up to around 80° C.;
(3) mixing water, phenoxyethanol, chlorphenesin, and butyleneglycol to form an aqueous phase;
(4) heating the aqueous phase up to around 80° C.;
(5) adding the aqueous phase into the oil phase followed by mixing them to obtain an O/W emulsion; and
(6) mixing xanthan gum, glycerin and water to the emulsion, followed by cooling the mixture down to room temperature.

(D) Comparative Examples 3-4

(1) mixing 2-oleamido-1,3-octanediol, ethylhexyl palmitate, PG-5 oleate, and mono glyceryl oleate to form an oil phase;
(2) heating the oil phase up to around 80° C.;
(3) mixing water and propyleneglycol, to form an aqueous phase;
(4) heating the aqueous phase up to around 80° C.;
(5) adding the aqueous phase into the oil phase followed by mixing them to obtain an O/W emulsion; and
(6) cooling the mixture down to room temperature.

The numerical values for the amounts of the components shown in Table 1 are all based on "% by weight" as active raw materials.

TABLE 1

|  | Ex. 1 | Ex. 2 | Comp. 1 | Comp. 2 | Comp. 3 | Comp. 4 |
| --- | --- | --- | --- | --- | --- | --- |
| 2-Oleamido-1,3-octanediol*[1] | 0.1 | 0.1 | 0.1 | 0.1 | 0.1 | 0.1 |
| Ethylhexylpalmitate | 1 | 1 | 1 | 1 | 1 | 1 |
| PG-5 Laurate*[2] | 1 | — | — | 1.1 | — | — |
| PG-5 Oleate*[3] | — | 1 | — | — | 1.75 | 1.75 |
| Mono-glyceryl oleate*[4] | — | — | — | — | 0.5 | 0.5 |
| Na N-stearoyl-N-methyl-taurate | 0.1 | 0.1 | 1.1 | — | — | — |
| Preservative | 0.8 | 0.8 | 0.8 | 0.8 | — | — |
| Xanthan gum | 0.1 | 0.1 | 0.1 | 0.1 | — | — |
| Glycerin | 10.0 | 10.0 | 10.0 | 10.0 | — | — |
| Butylene glycol | 8.5 | 8.5 | 8.5 | 8.5 | — | — |
| Propylene glycol | — | — | — | — | 0.75 | 0.75 |
| Water | q.s. 100 | q.s. 100 | q.s. 100 | q.s. 100 | q.s. 100 | q.s. 100 |

*[1]Mexanzyl GZ (Chimex)
*[2]Sunsoft A-121-E (Taiyo Kagaku)
*[3]Sunsoft A-171E-C (Taiyo Kagaku)
*[4]Sunsoft O-30S (Taiyo Kagaku)

The aspect, turbidity and pH of the obtained O/W emulsions according to Examples 1-2 and Comparative Examples 1-4 are shown in Table 2.

The aspect was based on visual observation.

The turbidity was based on the measurement with a 2100Q (HACH) with a round cell (25 mm in diameter×60 mm height) and a tungsten filament lump.

TABLE 2

|  | Ex. 1 | Ex. 2 | Comp. 1 | Comp. 2 | Comp. 3 | Comp. 4 |
| --- | --- | --- | --- | --- | --- | --- |
| Aspect | Transparent Liquid | Transparent Liquid | White liquid | Translucent-White liquid | White turbid Liquid | White turbid Liquid |

TABLE 2-continued

|  | Ex. 1 | Ex. 2 | Comp. 1 | Comp. 2 | Comp. 3 | Comp. 4 |
|---|---|---|---|---|---|---|
| Turbidity (NTU) | 72.0 | 128 | Not Measurable | Not Measurable | Not Measurable | Not Measurable |

Examples 3-4 and Comparative Examples 5-6

The following compositions according to Examples 3-4, and Comparative Examples 5-6, shown in Table 3, were prepared by mixing the components shown in Table 3 as follows:

(E) Examples 3 and 4

(1) mixing 2-oleamido-1,3-octanediol, ethylhexyl palmitate, PG-5 laurate and PPG-6 decyltetradeceth-30 to form an oil phase;
(2) heating the oil phase up to around 80° C.;
(3) mixing water, Na methyl stearoyl taurate, phenoxyethanol, butyleneglycol and citric acid, to form an aqueous phase;
(4) heating the aqueous phase up to around 80° C.;
(5) adding the aqueous phase into the oil phase followed by mixing them to obtain an O/W emulsion; and
(6) mixing xanthan gum, glycerin and water to the emulsion, followed by cooling the mixture down to room temperature.

(F) Comparative Examples 5 and 6

(1) mixing 2-oleamido-1,3-octanediol, ethylhexyl palmitate or isostearic acid, and PEG-60 hydrogenated castor oil to form an oil phase;
(2) heating the oil phase up to around 80° C.;
(3) mixing water and butylene glycol, in addition to, if used, citric acid or ethanol, to form an aqueous phase;
(4) heating the aqueous phase up to around 80° C.;
(5) adding the aqueous phase into the oil phase followed by mixing them to obtain an O/W emulsion; and
(6) cooling the mixture down to room temperature.

The numerical values for the amounts of the components shown in Table 3 are all based on "% by weight" as active raw materials.

TABLE 3

|  | Ex. 3 | Ex. 4 | Comp. 5 | Comp. 6 |
|---|---|---|---|---|
| 2-Oleamido-1,3-octanediol*¹ | 0.1 | 0.5 | 0.1 | 0.5 |
| Ethylhexylpalmitate | 1 | 3 | 1 | — |
| PG-5 Laurate*² | 1 | 3 | — | — |
| Na N-stearoyl-N-methyl-taurate | 0.1 | 0.2 | 0.1 | — |
| Isostearic acid | — | — | — | 0.7 |
| PPG-6 Decyltetradeceth-30 | 0.1 | 0.3 | — | — |
| PEG-60 Hydrogenated castor oil | — | — | 1 | 1 |
| Preservative | 0.5 | 0.5 | 0.5 | 0.5 |
| Xanthan gum | 0.1 | 0.1 | — | — |
| Glycerin | 10.0 | 10.0 | — | — |
| Butylene glycol | 8.5 | 8.5 | 8.5 | 10.0 |
| Ethanol | — | — | — | 7.0 |
| Citric acid | 0.01 | 0.01 | 0.01 | — |
| Water | q.s. 100 | q.s. 100 | q.s. 100 | q.s. 100 |

*¹Mexanzyl GZ (Chimex)
*²Sunsoft A-121-E (Taiyo Kagaku)

The aspect, turbidity, pH and stability of the obtained O/W emulsions according to Examples 1, 3 and 4, and Comparative Examples 3 and 4 are shown in Table 4.

The aspect was based on the visual observation of the emulsion.

The turbidity was based on the measurement of the emulsion with a 2100Q (HACH) having a round cell (25 mm in diameter×60 mm height) and a tungsten filament lump.

The stability was based on the visual observation of the aspect of the emulsion after maintaining the emulsion at 4° C., room temperature (RT: 25° C.), and 45° C. for 1 week.

TABLE 4

|  | Ex. 1 | Ex. 3 | Ex. 4 | Comp. 5 | Comp. 6 |
|---|---|---|---|---|---|
| Aspect | Transparent Liquid | Transparent Liquid | Transparent Liquid | Turbid Liquid | Turbid Liquid |
| Turbidity (NTU) | 72.0 | 54.0 | 70.6 | Not Measurable | 325 |
| pH | 4.5 | 4.5 | 4.5 | 4 | 5 |
| 4° C. Stability | Good | Good | Good | Good | Fair |
| RT Stability | Good | Good | Good | Poor | Poor |
| 45° C. Stability | Fair | Good | Fair | Poor | Poor |

Good: No change
Fair: Slightly foggy and/or while line on the wall
Poor: Foggy and/or creamy It is recognized that the compositions according to Examples 1-4 have transparent aspects, while the compositions according to Comparative Examples 5-6 have white or translucent aspects.

It is also recognized that the compositions according to Examples 1, 3 and 4 are more stable than the compositions according to Comparative Examples 5 and 6 over time, in particular even at room temperature or higher.

The invention claimed is:

1. A composition in the form of a nano- or microemulsion, comprising:
   (a) at least one oil;
   (b) at least one nonionic surfactant with an HLB (Hydrophilic Lipophilic Balance) value ranging from about 8.0 to about 14.0 that is fluid at a temperature less than or equal to 45° C., chosen from the esters of at least one polyol chosen from polyglycerols comprising from 2 to 12 glycerol units, and of at least one fatty acid comprising at least one saturated or unsaturated, linear or branched $C_8$-$C_{22}$ alkyl chain;
   (c) at least one ceramide compound;
   (d) at least one anionic surfactant; and
   (e) water,
   wherein the at least one nonionic surfactant with an HLB value ranging from about 8.0 to about 14.0 is chosen from:
      polyglyceryl monolaurate or dilaurate comprising 3 to 6 glycerol units;
      polyglyceryl mono(iso)stearate comprising 3 to 6 glycerol units;
      polyglyceryl monooleate comprising 3 to 6 glycerol units; or
      polyglyceryl dioleate comprising 3 to 6 glycerol units.

2. The composition according to claim 1, wherein the at least one oil is chosen from oils with a molecular weight below about 600 g/mol.

3. The composition according to claim 1, wherein the at least one oil is present in an amount ranging from about 0.1% to about 30% by weight, relative to the total weight of the composition.

4. The composition according to claim 1, wherein the at least one nonionic surfactant with an HLB value ranging from about 8.0 to about 14.0 is present in an amount ranging from about 0.1% to about 30% by weight, relative to the total weight of the composition.

5. The composition according to claim 1, wherein the at least one nonionic surfactant with an HLB value ranging from about 8.0 to about 14.0 and the at least one oil are present in a weight ratio of about 2 or less.

6. The composition according to claim 1, wherein the at least one ceramide compound is chosen from formula (I) below:

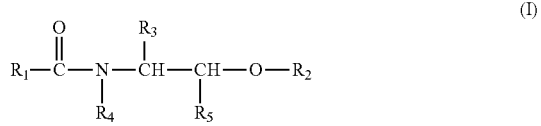

wherein:
R$_1$ is chosen from:
a saturated or unsaturated, linear or branched C$_1$-C$_{50}$ hydrocarbon radical, wherein the radical is substituted by at least one hydroxyl group optionally esterified by an acid R$_7$COOH, wherein R$_7$ is optionally mono- or polyhydroxylated, saturated or unsaturated, linear or branched C$_1$-C$_{35}$ hydrocarbon radical, further wherein the hydroxyl or hydroxyls of the R$_7$ radical is esterified by an optionally mono- or polyhydroxylated, saturated or unsaturated, linear or branched C$_1$-C$_{35}$ fatty acid;
an R"—(NR—CO)—R' radical, wherein R is chosen from a hydrogen atom or a mono- or polyhydroxylated C$_1$-C$_{20}$ hydrocarbon radical, R' and R" are hydrocarbon radicals, the sum of the carbon atoms ranging from 9 to 30, and R' is a divalent radical; or
an R$_8$—O—CO—(CH$_2$)$_p$ radical, wherein R$_8$ is a C$_1$-C$_{20}$ hydrocarbon radical and p is an integer ranging from 1 to 12;
R$_2$ is chosen from a hydrogen atom, a radical of saccharide type, a (glycosyl)$_n$, (galactosyl)$_m$ or sulphogalactosyl radical, a sulphate or phosphate residue, or a phosphorylethylamine radical or a phosphorylethylammonium radical, wherein n is an integer ranging from 1 to 4 and m is an integer ranging from 1 to 8;
R$_3$ is chosen from a hydrogen atom or a hydroxylated or nonhydroxylated and saturated or unsaturated C$_1$-C$_{33}$ hydrocarbon radical, wherein the hydroxyl or hydroxyls are esterified by an inorganic acid or an acid R$_7$COOH, with R$_7$ having the same meanings as above, optionally the hydroxyl is etherified by a (glycosyl)$_n$, (galactosyl)$_m$, sulphogalactosyl, phosphorylethylamine, or phosphorylethylammonium radical, wherein n is an integer ranging from 1 to 4 and m is an integer ranging from 1 to 8, or optionally R$_3$ is substituted by at least one C$_1$-C$_{14}$ alkyl radical;
R$_4$ is chosen from a hydrogen atom, a methyl or ethyl radical, an optionally hydroxylated, saturated or unsaturated, linear or branched C$_3$-C$_{50}$ hydrocarbon radical, or a —CH$_2$—CHOH—CH$_2$—O—R$_6$ radical, wherein R$_6$ is chosen from a C$_{10}$-C$_{26}$ hydrocarbon radical, or an R$_8$—O—CO—(CH$_2$)$_p$ radical, wherein R$_8$ is a C$_1$-C$_{20}$ hydrocarbon radical and p is an integer ranging from 1 to 12; and
R$_5$ is chosen from a hydrogen atom or an optionally mono- or polyhydroxylated, saturated or unsaturated, linear or branched C$_1$-C$_{30}$ hydrocarbon radical, optionally the hydroxyl is etherified by a (glycosyl)$_n$, (galactosyl)$_m$, sulphogalactosyl, phosphorylethylamine, or phosphorylethylammonium radical, wherein n is an integer ranging from 1 to 4 and m is an integer ranging from 1 to 8; and
further wherein, when R$_3$ and R$_5$ are hydrogen or when R$_3$ is hydrogen and R$_5$ is methyl, then R$_4$ is not chosen from a hydrogen atom or a methyl or ethyl radical.

7. The composition according to claim 6, wherein R$_3$ is a C$_{15}$-C$_{26}$ α-hydroxyalkyl radical and the hydroxyl group is optionally esterified by a C$_{16}$-C$_{30}$ α-hydroxy acid.

8. The composition according to claim 1, wherein the at least one ceramide compound is chosen from 2-N-linoleoylaminooctadecane-1,3-diol, 2-N-oleoylaminooctadecane-1,3-diol, 2-N-palmitoylaminooctadecane-1,3-diol, 2-N-stearoylaminooctadecane-1,3-diol, 2-N-behenoylaminooctadecane-1,3-diol, 2-N-[2-hydroxypalmitoyl]aminooctadecane-1,3-diol, 2-N-stearoylaminoocta-decane-1,3,4-triol, 2-N-palmitoylaminohexadecane-1,3-diol, or mixtures thereof.

9. The composition according to claim 1, wherein the at least one ceramide compound is chosen from bis(N-hydroxyethyl-N-cetyl)malonamide, the N-(2-hydroxyethyl)-N-(3-cetyloxy-2-hydroxypropyl)amide of cetylic acid, or N-docosanoyl-N-methyl-D-glucamine.

10. The composition according to claim 1, wherein the at least one ceramide compound is present in an amount ranging from about 0.01% to about 20% by weight, relative to the total weight of the composition.

11. The composition according to claim 1, wherein the weight ratio of the at least one nonionic surfactant with an HLB value ranging from about 8.0 to about 14.0 to the at least one ceramide compound is about 15 or less.

12. The composition according to claim 1, wherein the at least one anionic surfactant is chosen from anionic derivatives of proteins of vegetable origin or of silk proteins, phosphates and alkyl phosphates, carboxylates, sulphosuccinates, amino acid derivatives, alkyl sulphates, alkyl ether sulphates, sulphonates, isethionates, taurates, alkyl sulphoacetates, polypeptides, anionic derivatives of alkyl polyglucosides, or mixtures thereof.

13. The composition according to claim 1, wherein the at least one anionic surfactant is chosen from taurates or glutamates.

14. The composition according to claim 1, wherein the at least one anionic surfactant is present in an amount ranging from about 0.01% to about 20% by weight, relative to the total weight of the composition.

15. The composition according to claim 1, wherein the water is present in an amount ranging from about 40% to about 90% by weight, relative to the total weight of the composition.

16. The composition according to claim 1, further comprising at least one cationic or amphoteric surfactant.

17. The composition according to claim 1, wherein the composition has a turbidity of about 300 NTU or less.

18. The composition according to claim 1, wherein the composition is a cosmetic composition.

19. A cosmetic and/or non-therapeutic process for treating the skin, hair, mucous membranes, nails, eyelashes, eyebrows and/or scalp, comprising:
  applying to the skin, hair, mucous membranes, nails, eyelashes, eyebrows, and/or scalp a composition in the form of a nano- or micro-emulsion, the composition comprising:
    (a) at least one oil;
    (b) at least one nonionic surfactant with an HLB (Hydrophilic Lipophilic Balance) value ranging from about 8.0 to about 14.0 that is fluid at a temperature less than or equal to 45° C., chosen from the esters of at least one polyol chosen from polyglycerols comprising from 2 to 12 glycerol units, and of at least one fatty acid comprising at least one saturated or unsaturated, linear or branched $C_8$-$C_{22}$ alkyl chain;
    (c) at least one ceramide compound;
    (d) at least one anionic surfactant; and
    (e) water;
  wherein the at least one nonionic surfactant with an HLB value ranging from about 8.0 to about 14.0 is chosen from:
    polyglyceryl monolaurate or dilaurate comprising 3 to 6 glycerol units;
    polyglyceryl mono(iso)stearate comprising 3 to 6 glycerol units;
    polyglyceryl monooleate comprising 3 to 6 glycerol units; or
    polyglyceryl dioleate comprising 3 to 6 glycerol units.

* * * * *